(12) United States Patent
Dunkel et al.

(10) Patent No.: US 7,977,363 B2
(45) Date of Patent: *Jul. 12, 2011

(54) BIPHENYL-THIAZOLO-CARBOXAMIDES

(75) Inventors: Ralf Dunkel, Lyons (FR); Hans-Ludwig Elbe, Wuppertal (DE); Jörg Nico Greul, Leichlingen (DE); Benoit Hartmann, Foy les Lyons (FR); Herbert Gayer, Monheim (DE); Thomas Seitz, Langenfeld (DE); Ulrike Wachendorff-Neumann, Neuwied (DE); Peter Dahmen, Neuss (DE); Karl-Heinz Kuck, Langenfeld (DE)

(73) Assignee: Bayer Cropscience AG, Monheim (DE)

( * ) Notice: Subject to any disclaimer, the term of this patent is extended or adjusted under 35 U.S.C. 154(b) by 606 days.

This patent is subject to a terminal disclaimer.

(21) Appl. No.: 11/661,100

(22) PCT Filed: Aug. 13, 2005

(86) PCT No.: PCT/EP2005/008837
§ 371 (c)(1),
(2), (4) Date: Feb. 15, 2008

(87) PCT Pub. No.: WO2006/024387
PCT Pub. Date: Mar. 9, 2006

(65) Prior Publication Data
US 2008/0242708 A1 Oct. 2, 2008

(30) Foreign Application Priority Data
Aug. 27, 2004 (DE) .................... 10 2004 041 530

(51) Int. Cl.
*A61K 31/426* (2006.01)
*C07D 277/20* (2006.01)
(52) U.S. Cl. .................. 514/365; 548/146; 548/200
(58) Field of Classification Search .................. 548/146, 548/200; 514/365
See application file for complete search history.

(56) References Cited

U.S. PATENT DOCUMENTS

| | | | |
|---|---|---|---|
| 3,547,917 A | 12/1970 | Kulka et al. | |
| 5,330,995 A | 7/1994 | Eicken et al. | |
| 5,416,103 A | 5/1995 | Eicken et al. | |
| 5,438,070 A | 8/1995 | Eicken et al. | |
| 5,633,218 A | 5/1997 | Spedding et al. | |
| 5,998,450 A | 12/1999 | Eicken et al. | |
| 7,098,227 B2 | 8/2006 | Dunkel et al. | |
| 7,388,097 B2 * | 6/2008 | Elbe et al. ................. | 548/136 |
| 7,470,793 B2 * | 12/2008 | Dunkel et al. ............. | 548/181 |
| 2005/0124815 A1 | 6/2005 | Elbe et al. | |
| 2006/0116414 A1 | 6/2006 | Dunkel et al. | |
| 2006/0128769 A1 | 6/2006 | Dunkel et al. | |
| 2007/0060579 A1 | 3/2007 | Wachendorff-Neumann et al. | |
| 2009/0076113 A1 | 3/2009 | Dunkel et al. | |
| 2009/0105316 A1 | 4/2009 | Dunkel et al. | |

FOREIGN PATENT DOCUMENTS

| | | |
|---|---|---|
| EP | 0 371 950 A2 | 6/1990 |
| EP | 0 371 950 A3 | 6/1990 |
| EP | 0 545 099 A2 | 6/1993 |
| EP | 0 545 099 A3 | 6/1993 |
| EP | 0 589 301 A1 | 3/1994 |
| EP | 0 589 313 A1 | 3/1994 |
| EP | 1 110 454 A2 | 6/2001 |
| EP | 1 110 454 A3 | 6/2001 |
| JP | 08-176112 A | 7/1996 |
| JP | 2001-302605 A | 10/2001 |
| WO | WO 96/37494 A1 | 11/1996 |
| WO | WO 97/08148 A1 | 3/1997 |
| WO | WO 98/25923 A1 | 6/1998 |
| WO | WO 01/90084 A1 | 11/2001 |
| WO | WO 02/059086 A1 | 8/2002 |
| WO | WO 03/066609 A1 | 8/2003 |
| WO | WO 03/066610 A1 | 8/2003 |
| WO | WO 03/070705 A1 | 8/2003 |
| WO | WO 2004/035555 A1 | 4/2004 |
| WO | WO 2005/034628 A1 | 4/2005 |
| WO | WO 2005/041653 A2 | 5/2005 |
| WO | WO 2005/041653 A3 | 5/2005 |

OTHER PUBLICATIONS

English language Abstract of Japanese Patent Publication No. JP 08-176112 A, espacenet database—Worldwide, (1996).
Office Action mailed Sep. 21, 2006, in U.S. Appl. No. 10/530,513, Dunkel et al., with a 35 U.S.C. § 371(c) date of Aug. 22, 2005.
Office Action mailed May 9, 2007, in U.S. Appl. No. 10/530,513, Dunkel et al., with a 35 U.S.C. § 371(c) date of Aug. 22, 2005. Office Action mailed Nov. 16, 2007, in U.S. Appl. No. 10/530,513, Dunkel et al., with a 35 U.S.C. § 371(c) date of Aug. 22, 2005.
Office Action mailed Sep. 9, 2008, in U.S. Appl. No. 10/530,513, Dunkel et al., with a 35 U.S.C. § 371(c) date of Aug. 22, 2005.
Office Action mailed Jun. 10, 2009, in U.S. Appl. No. 10/530,513, Dunkel et al., with a 35 U.S.C. § 371(c) date of Aug. 22, 2005.
Office Action mailed Dec. 29, 2009, in U.S. Appl. No. 10/530,513, Dunkel et al., with a 35 U.S.C. § 371(c) date of Aug. 22, 2005.
Office Action mailed Feb. 17, 2010, in U.S. Appl. No. 11/661,092, Dunkel et al., with a 35 U.S.C. § 371(c) date of Oct. 8, 2008.

(Continued)

*Primary Examiner* — Golam M Shameem
(74) *Attorney, Agent, or Firm* — Sterne, Kessler, Goldstein & Fox, P.L.L.C.

(57) ABSTRACT

Novel biphenyl thiazole carboxamides of Formula (I)

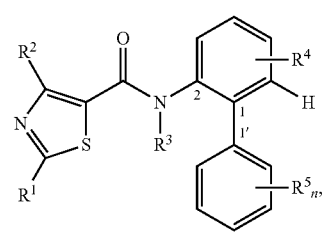

where
$R^1$, $R^2$, $R^3$, $R^4$, $R^5$ and n have the meanings specified in the description,
several methods for the manufacture of these substances and their use for combating undesired microorganisms, as well as novel intermediate products and their manufacture.

34 Claims, No Drawings

OTHER PUBLICATIONS

Office Action mailed Dec. 31, 2009, in U.S. Appl. No. 12/571,951, Dunkel et al., with a filed of Oct. 1, 2009.

Phillips, W.G. and Rejda-Heath, J.M., "Thiazole Carboxanilide Fungicides: A New Structure-Activity Relationship for Succinate Dehydrogenase Inhibitors," *Pestic. Sci.* 38:1-7, Wiley and Sons (1993).

Patent Abstracts of Japan, English language abstract for JP 2001-302605 (listed on accompanying PTO/SB/08A as document FP12).
International Search Report for International Application No. PCT/EP2005/008837, European Patent Office, Netherlands, mailed on Mar. 17, 2006.
English language translation of WO 2005/041653 A2, 126 pages (listed on accompanying PTO/SB/08A as document FP20).

* cited by examiner

BIPHENYL-THIAZOLO-CARBOXAMIDES

This application is a National Stage of International Application No. PCT/EP2005/008837, filed Aug. 13, 2005, which claims the benefit of German Patent Application No. 10 2004 041 530.7, filed Aug. 27, 2004.

The present invention relates to novel biphenyl thiazole carboxamides, several methods for their manufacture and their use for combating undesired microorganisms.

It is already known that numerous carboxamides possess fungicidal properties (see e.g. WO 03/070705, WO 97/08148 and JP-A 2001-302605). Therefore, a multitude of biphenyl carboxamides have already been identified that can be substituted in the biphenyl portion, such as e.g. N-(3',4'-dichloro-3-fluoro-1,1'-biphenyl-2-yl)-1-methyl-3-(trifluoromethyl)-1H-pyrazole-4-carboxamide from WO 03/070705, N-(5-fluoro-4'-methylbiphenyl-2-yl)-2-methyl-4-(trifluoromethyl)-1,3-thiazole-5-carboxamide from WO 97/08148 and N-(4'-methoxy-6-methylbiphenyl-2-yl)-2-methyl-4-(trifluoromethyl)-1,3-thiazole-5-carboxamide from JP 2001-302605. The efficacy of these substances is good, however in most cases, e.g. with low application rates, it leaves something to be desired.

Novel biphenyl thiazole carboxamides of Formula (I)

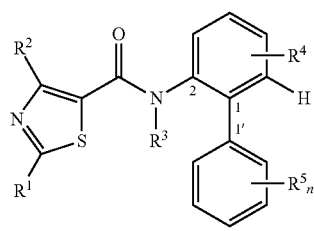

were found, where $R^1$ stands for hydrogen, halogen, amino, $C_1$-$C_4$-alkylamino, di-($C_1$-$C_4$-alkyl)amino, cyano, $C_1$-$C_4$-alkyl or $C_1$-$C_4$-halogenalkyl with 1 to 5 halogen atoms, $R^2$ stands for halogen, $C_1$-$C_4$-alkyl or $C_1$-$C_4$-halogenalkyl with 1 to 5 halogen atoms, $R^3$ stands for hydrogen, $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-halogenalkyl, $C_1$-$C_4$-halogenalkylthio, $C_1$-$C_4$-halogenalkylsulphinyl, $C_1$-$C_4$-halogenalkylsulphonyl, halogen-$C_1$-$C_4$-alkoxy-$C_1$-$C_4$-alkyl, $C_3$-$C_8$-halogencycloalkyl, each with 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halogen-($C_1$-$C_3$-alkyl)carbonyl-$C_1$-$C_3$-alkyl, halogen-($C_1$-$C_3$-alkoxy)carbonyl-$C_1$-$C_3$-alkyl, each with 1 to 13 fluorine, chlorine and/or bromine atoms; ($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl)carbonyl; ($C_1$-$C_6$-halogenalkyl)carbonyl, ($C_1$-$C_6$-halogenalkoxy)carbonyl, (halogen-$C_1$-$C_4$-alkoxy-$C_1$-$C_4$-alkyl)carbonyl, ($C_3$-$C_8$-halogen cycloalkyl)carbonyl, each with 1 to 9 fluorine, chlorine and/or bromine atoms; or —C(=O)C(=O)R$^6$, —CONR$^7$R$^8$ or —CH$_2$NR$^9$R$^{10}$, $R^4$ stands for halogen, $C_1$-$C_4$-alkyl, $C_1$-$C_4$-alkoxy, $C_1$-$C_4$-alkylthio or $C_1$-$C_4$-halogenalkyl with 1 to 9 fluorine, chlorine and/or bromine atoms, $R^5$ stands for halogen, cyano, nitro, amino, hydroxy, formyl, carboxy, carbamoyl, thiocarbamoyl, $C_1$-$C_8$-alkyl, $C_2$-$C_6$-alkenyl, $C_1$-$C_8$-alkoxy, $C_2$-$C_6$-alkenyloxy, $C_1$-$C_8$-alkylthio, $C_1$-$C_8$-alkyl sulphinyl, $C_1$-$C_8$-alkylsulphonyl, $C_1$-$C_8$-hydroxyalkyl, $C_1$-$C_8$-oxoalkyl, $C_1$-$C_8$-alkoxyalkyl, $C_1$-$C_8$-alkylthioalkyl, $C_1$-$C_8$-dialkoxyalkyl, $C_1$-$C_6$-alkylamino, di($C_1$-$C_6$-alkyl)amino, ($C_1$-$C_6$-alkyl)carbonyl, ($C_1$-$C_6$-alkyl)carbonyloxy, ($C_1$-$C_6$-alkoxy)carbonyl, ($C_1$-$C_6$-alkyl)amino carbonyl, di($C_1$-$C_6$-alkyl)amino carbonyl, ($C_1$-$C_6$-alkyl)carbonyl amino, ($C_1$-$C_6$-alkyl)-carbonyl($C_1$-$C_6$-alkyl)amino, ($C_2$-$C_6$-alkenyl)carbonyl, ($C_2$-$C_6$-alkinyl)carbonyl, $C_3$-$C_6$-cycloalkyl, $C_3$-$C_6$-cycloalkyloxy, or for $C_1$-$C_6$-halogenalkyl, $C_1$-$C_6$-halogenalkoxy, $C_1$-$C_6$-halogen alkylthio, $C_1$-$C_6$-halogenalkylsulphinyl or $C_1$-$C_6$-halogenalkylsulphonyl, each with 1 to 13 halogen atoms, $C_2$-$C_6$-halogenalkenyl, $C_2$-$C_6$-halogenalkenyloxy, each with 1 to 11 of the same or different halogen atoms, $R^5$ further stands for $C_2$-$C_5$-alkenylene possibly substituted once or twice by halogen, $C_1$-$C_4$-alkyl or $C_1$-$C_4$-halogenalkyl with 1 to 5 halogen atoms, if two $R^5$ moieties are in ortho position to each other, n stands for 2, 3, 4 or 5, whereby the $R^5$ moieties can be the same or different, $R^6$ stands for hydrogen, $C_1$-$C_8$-alkyl, $C_1$-$C_8$-alkoxy, $C_1$-$C_4$-alkoxy-$C_1$-$C_4$-alkyl, $C_3$-$C_8$-cycloalkyl; $C_1$-$C_6$-halogenalkyl, $C_1$-$C_6$-halogenalkoxy, halogen-$C_1$-$C_4$-alkoxy-$C_1$-$C_4$-alkyl, $C_3$-$C_8$-halogen cycloalkyl, each with 1 to 9 fluorine, chlorine and/or bromine atoms, $R^7$ and $R^8$, independently of one another, each stand for hydrogen, $C_1$-$C_8$-alkyl, $C_1$-$C_4$-alkoxy-$C_1$-$C_4$-alkyl, $C_3$-$C_8$-cycloalkyl; $C_1$-$C_8$-halogenalkyl, halogen-$C_1$-$C_4$-alkoxy-$C_1$-$C_4$-alkyl, $C_3$-$C_8$-halogencycloalkyl, each with 1 to 9 fluorine, chlorine and/or bromine atoms, $R^7$ and $R^8$, together with the nitrogen atom to which they are bonded, further form a saturated heterocycle with 5 to 8 ring atoms, possibly substituted once or twice, identically or variously, by halogen or $C_1$-$C_4$-alkyl, in which the heterocycle can contain 1 or 2 additional, non-adjacent heteroatoms from the group of hydrogen, sulphur or NR$^{11}$, $R^9$ and $R^{10}$, independently of one another, stand for hydrogen, $C_1$-$C_8$-alkyl, $C_3$-$C_8$-cycloalkyl; $C_1$-$C_8$-halogenalkyl, $C_3$-$C_8$-halogencycloalkyl, each with 1 to 9 fluorine, chlorine and/or bromine atoms, $R^9$ and $R^{10}$, together with the nitrogen atom to which they are bonded, further form a saturated heterocycle with 5 to 8 ring atoms, possibly substituted once or twice, identically or variously, by halogen or $C_1$-$C_4$-alkyl, in which the heterocycle can contain 1 or 2 additional, non-adjacent heteroatoms from the group of hydrogen, sulphur or NR$^{11}$, $R^{11}$ stands for hydrogen or $C_1$-$C_6$-alkyl.

Furthermore, it was found that one can obtain biphenyl thiazole carboxamides of Formula (I), by (a) Reacting Carboxylic Acid Derivatives of Formula (I)

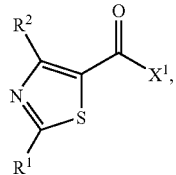

where
R¹ and R² have the meanings specified above and
X¹ stands for halogen or hydroxy,
with biphenyl amines of Formula (III)

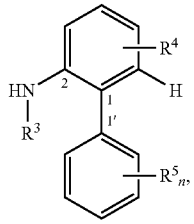
(III)

where R³, R⁴, R⁵ and n have the meanings specified above,
in the presence of a catalyst if applicable, in the presence of a condensation agent if applicable, in the presence of an acid binding agent if applicable and in the presence of a diluent if applicable, or (b) by reacting halogen carboxamides of Formula (IV)

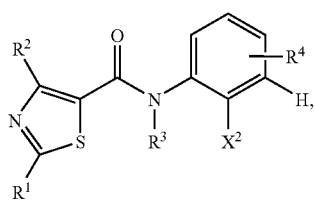
(IV)

where
R¹, R², R³ and R⁴ have the meanings specified above,
X² stands for bromine, iodine or trifluoromethylsulphonate,
with boronic acid derivatives of Formula (V)

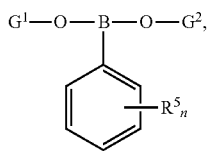
(V)

where
R⁵ and n have the meanings specified above and
G¹ and G² each stand for hydrogen or jointly stand for tetramethylethylene, in the presence of a catalyst, in the presence of an acid binding agent if applicable and in the presence of a diluent if applicable, or (c) by reacting boronic acid derivatives of Formula (VI)

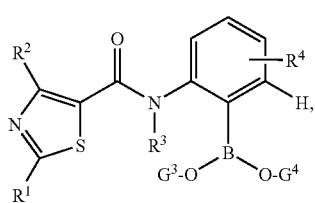
(VI)

where
R¹, R², R³ and R⁴ have the meanings specified above,
G³ and G⁴ each stand for hydrogen or jointly stand for tetramethylethylene,
with phenyl derivatives of Formula (VII)

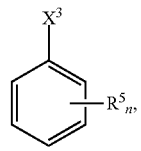
(VII)

where
R⁵ and n have the meanings specified above and
X³ stands for chlorine, bromine, iodine or trifluoromethylsulphonate,
in the presence of a catalyst, in the presence of an acid binding agent if applicable and in the presence of a diluent if applicable, or (d) by reacting halogen carboxamides of Formula (IV)

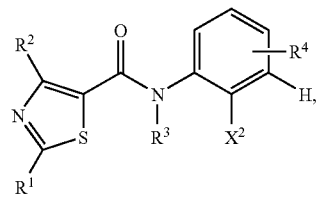
(IV)

where
R¹, R², R³ and R⁴ have the meanings specified above,
X² stands for bromine, iodine or trifluoromethylsulphonate,
with phenyl derivatives of Formula (VII)

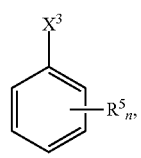
(VII)

where
R⁵ and n have the meanings specified above and
X³ stands for chlorine, bromine, iodine or trifluoromethylsulphonate,
in the presence of a palladium or nickel catalyst and in the presence of 4,4,4',4',5,5,5',5'-octamethyl-2,2'-bis-1,3,2-dioxaborolane, in the presence of an acid binding agent if applicable and in the presence of a diluent if applicable, or (e) by reacting biphenyl thiazole carboxamides of Formula (I-a)

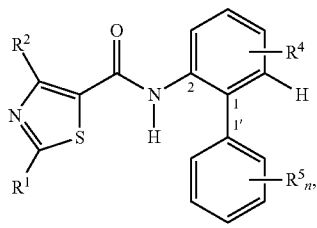
(I-a)

where
$R^1$, $R^2$, $R^4$, $R^5$ and n have the meanings specified above, with halogenides of formula (VIII)

$$R^{3,4}-X^4 \quad (VIII),$$

where
$R^{3,4}$ stands for $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-halogenalkyl, $C_1$-$C_4$-halogenalkylthio, $C_1$-$C_4$-halogenalkylsulphinyl, $C_1$-$C_4$-halogenalkylsulphonyl, halogen-$C_1$-$C_4$-alkoxy-$C_1$-$C_4$-alkyl, $C_3$-$C_8$-halogencycloalkyl, each with 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halogen-($C_1$-$C_3$-alkyl)carbonyl-$C_1$-$C_3$-alkyl, halogen-($C_1$-$C_3$-alkoxy)carbonyl-$C_1$-$C_3$-alkyl, each with 1 to 13 fluorine, chlorine and/or bromine atoms;

($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl)carbonyl; ($C_1$-$C_6$-halogenalkyl)carbonyl, ($C_1$-$C_6$-halogenalkoxy)-carbonyl, (halogen-$C_1$-$C_4$-alkoxy-$C_1$-$C_4$-alkyl)carbonyl, ($C_3$-$C_8$-halogencycloalkyl)carbonyl, each with 1 to 9 fluorine, chlorine and/or bromine atoms; or —C(=O)C(=O)$R^6$, —CONR$^7$R$^8$ or —CH$_2$NR$^9$R$^{10}$, $R^6$, $R^7$, $R^8$, $R^9$ and $R^{10}$ have the meanings specified above, $X^4$ stands for chlorine, bromine or iodine,
in the presence of a base and in the presence of a diluent.

Finally, it was found that the novel biphenyl thiazole carboxamides of formula (I) possess very good microbicidal properties and can be employed for combating undesired microorganisms as well as in the areas of plant protection and material protection.

The compounds according to the invention can possibly occur as mixtures of various possible isomer forms, particularly of stereoisomers, such as e.g. E-isomers and Z-isomers, threo isomers and erythro isomers, as well as optical isomers; however they can possibly occur as tautomers as well. The claims of this patent cover the E-isomers and the Z-isomers, as well as the threo isomers and erythro isomers, and the optical isomers, any mixtures of these isomers, and the possible tautomer forms.

The biphenyl thiazole carboxamides according to the invention are generally defined by Formula (I). Preferred moiety definitions of the preceding and following formulas are specified in the following section. These definitions are equally valid for the final products of Formula (I) as well as for all intermediate products.

$R^1$ preferably stands for hydrogen, fluorine, chlorine, bromine, amino, $C_1$-$C_4$-alkylamino, di($C_1$-$C_4$-alkyl)amino, cyano, methyl, ethyl or $C_1$-$C_2$-halogenalkyl with 1 to 5 fluorine, chlorine and/or bromine atoms.

$R^1$ particularly preferably stands for hydrogen, fluorine, chlorine, bromine, amino, methylamino, dimethylamino, cyano, methyl, ethyl, trifluoromethyl, difluoromethyl, difluorochloromethyl or trichloromethyl.

$R^1$ quite particularly preferably stands for hydrogen, fluorine, chlorine, bromine, amino, methylamino, dimethylamino, methyl, trifluoromethyl, difluoromethyl or trichloromethyl.

$R^1$ especially preferably stands for amino, chlorine, methylamino, dimethylamino, methyl or trifluoromethyl.

$R^2$ preferably stands for fluorine, chlorine, bromine, methyl, ethyl or $C_1$-$C_2$-halogenalkyl with 1 to 5 fluorine, chlorine and/or bromine atoms.

$R^2$ particularly preferably stands for fluorine, chlorine, bromine, methyl, ethyl, 1-fluoroethyl, trifluoromethyl, difluoromethyl, difluorochloromethyl or trichloromethyl.

$R^2$ quite particularly preferably stands for fluorine, chlorine, bromine, methyl, trifluoromethyl, difluoromethyl or trichloromethyl.

$R^2$ especially preferably stands for methyl, trifluoromethyl or difluoromethyl.

$R^3$ preferably stands for hydrogen, $C_1$-$C_6$-alkyl, $C_1$-$C_4$-alkylsulphinyl, $C_1$-$C_4$-alkylsulphonyl, $C_1$-$C_3$-alkoxy-$C_1$-$C_3$-alkyl, $C_3$-$C_6$-cycloalkyl; $C_1$-$C_4$-halogenalkyl, $C_1$-$C_4$-halogenalkylthio, $C_1$-$C_4$-halogenalkylsulphinyl, $C_1$-$C_4$-halogenalkylsulphonyl, halogen-$C_1$-$C_3$-alkoxy-$C_1$-$C_3$-alkyl, $C_3$-$C_8$-halogencycloalkyl, each with 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halogen-$C_1$-$C_3$-alkyl)carbonyl-$C_1$-$C_3$-alkyl, halogen-$C_1$-$C_3$-alkoxy)carbonyl-$C_1$-$C_3$-alkyl, each with 1 to 13 fluorine, chlorine and/or bromine atoms; ($C_1$-$C_6$-alkyl)carbonyl, ($C_1$-$C_4$-alkoxy)carbonyl, ($C_1$-$C_3$-alkoxy-$C_1$-$C_3$-alkyl)carbonyl, ($C_3$-$C_6$-cycloalkyl)carbonyl; ($C_1$-$C_4$-halogenalkyl)carbonyl, ($C_1$-$C_4$-halogenalkoxy)carbonyl, (halogen-$C_1$-$C_3$-alkoxy-$C_1$-$C_3$-alkyl)carbonyl, ($C_3$-$C_6$-halogencycloalkyl)carbonyl, each with 1 to 9 fluorine, chlorine and/or bromine atoms; or —C(=O)C(=O)$R^6$, —CONR$^7$R$^8$ or —CH$_2$NR$^9$R$^{10}$.

$R^3$ particularly preferably stands for hydrogen, methyl, ethyl, n- or iso-propyl, n-, iso-, sec- or tert-butyl, pentyl or hexyl, methylsulphinyl, ethylsulphinyl, n- or iso-propylsulphinyl, n-, iso-, sec- or tert-butylsulphinyl, methylsulphonyl, ethylsulphonyl, n- or iso-propylsulphonyl, n-, iso-, sec- or tert-butylsulphonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulphinyl, trifluoromethylsulphonyl, trifluoromethoxymethyl; formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —(CH$_2$)$_2$—CO—CH$_3$, —(CH$_2$)$_2$—CO—CH$_2$CH$_3$, —(CH$_2$)$_2$—CO—CH(CH$_3$)$_2$, —CH$_2$—CO$_2$CH$_3$, —CH$_2$—CO$_2$CH$_2$CH$_3$, —CH$_2$—CO$_2$CH(CH$_3$)$_2$, —(CH$_2$)$_2$—CO$_2$CH$_3$, —(CH$_2$)$_2$—CO$_2$CH$_2$CH$_3$, —(CH$_2$)$_2$—CO$_2$CH(CH$_3$)$_2$, —CH$_2$—CO—CF$_3$, —CH$_2$—CO—CCl$_3$, —CH$_2$—CO—CH$_2$CF$_3$, —CH$_2$—CO—CH$_2$CCl$_3$, —(CH$_2$)$_2$—CO—CH$_2$CF$_3$, —(CH$_2$)$_2$—CO—CH$_2$CCl$_3$, —CH$_2$—CO$_2$CH$_2$CF$_3$, —CH$_2$—CO$_2$CF$_2$CF$_3$, —CH$_2$—CO$_2$CH$_2$CCl$_3$, —CH$_2$—CO$_2$CCl$_2$CCl$_3$, —(CH$_2$)$_2$—CO$_2$CH$_2$CF$_3$, —(CH$_2$)$_2$—CO$_2$CF$_2$CF$_3$, —(CH$_2$)$_2$—CO$_2$CH$_2$CCl$_3$, —(CH$_2$)$_2$—CO$_2$CCl$_2$CCl$_3$; methyl carbonyl, ethyl carbonyl, n-propylcarbonyl, iso-propylcarbonyl, tert-butylcarbonyl, methoxycarbonyl, ethoxycarbonyl, tert-butoxycarbonyl, cyclopropylcarbonyl; trifluoromethylcarbonyl, trifluoromethoxycarbonyl, or —C(=O)C(=O)$R^6$, —CON$R^7R^8$ or —CH$_2$N$R^9R^{10}$.

$R^3$ quite particularly preferably stands for hydrogen, methyl, methoxymethyl, formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —C(=O)CHO, —C(=O)C(=O)CH$_3$, —C(=O)C(=O)CH$_2$OCH$_3$, —C(=O)CO$_2$CH$_3$, —C(=O)CO$_2$CH$_2$CH$_3$.

$R^4$ preferably stands for fluorine, where fluorine is particularly preferably in the 3-position or the 5-position, quite particularly preferably in the 5-position of the respective compound [see e.g. Formula (I)].

$R^4$ particularly preferably stands for chlorine, where chlorine is particularly preferably in the 4-position or 5-position, quite particularly preferably in the 4-position, as well as quite particularly preferably in the 5-position of the respective compound.

$R^4$ further preferably stands for trifluoromethyl, where trifluoromethyl is particularly preferably in the 4-position or 5-position of the respective compound.

$R^4$ further preferably stands for methoxy or methylthio, where methoxy or methylthio is particularly preferably in the 3-position or the 5-position, quite particularly preferably in the 5-position of the respective compound.

$R^4$ further preferably stands for methyl, where methyl is particularly preferably in the 4-position or 5-position, quite particularly preferably in the 4-position of the respective compound.

$R^4$ further preferably stands for iso-propyl, where iso-propyl is particularly preferably in the 4-position or 5-position, quite particularly preferably in the 5-position of the respective compound.

$R^5$ preferably stands for fluorine, chlorine, bromine, cyano, nitro, amino, hydroxy, formyl, methyl, ethyl, n- or iso-propyl, n-, iso-, sec- or tert-butyl, vinyl, allyl, methoxy, ethoxy, n- or iso-propoxy, vinyloxy, allyloxy, methylthio, ethylthio, n- or iso-propylthio, methylsulphinyl, ethylsulphinyl, n- or iso-propylsulphinyl, methylsulphonyl, ethylsulphonyl, n- or iso-propylsulphonyl, methoxymethyl, methoxyethyl, ethoxymethyl, ethoxyethyl, methylthiomethyl, methylthioethyl, ethylthiomethyl, ethylthioethyl, methylamino, ethyl amino, iso-propylamino, dimethylamino, diethylamino, dipropylamino, diisopropylamino, methyl carbonyl, ethyl carbonyl, methylaminocarbonyl, dimethylaminocarbonyl, methylcarbonylamino, methylcarbonylmethlyamino, cyclopropyl, cyclopropyloxy, trifluoromethyl, trichloromethyl, trifluoroethyl, difluoromethoxy, trifluoromethoxy, difluorochloromethoxy, trifluoroethoxy, difluoromethylthio, difluorochloromethylthio or trifluoromethylthio.

$R^5$ further preferably stands for $C_2$-$C_4$-alkenylene possibly substituted one or twice by fluorine, chlorine, bromine, methyl, ethyl, n- or iso-propyl, n-, iso-, sec- or tert-butyl or trifluoromethyl, if two $R^5$ moieties are in ortho position to each other.

$R^5$ particularly preferably stands for fluorine, chlorine, bromine, methyl, ethyl, n- or iso-propyl, n-, iso-, sec- or tert-butyl, methoxy, ethoxy, n- or iso-propoxy, methylthio, ethylthio, n- or iso-propylthio, methylsulphonyl, ethylsulphonyl, n- or iso-propylsulphonyl, methoxymethyl, methylthiomethyl, methylamino, ethyl amino, iso-propylamino, dimethylamino, diethylamino, diisopropylamino, methyl carbonyl, methylaminocarbonyl, dimethylaminocarbonyl, methylcarbonylamino, cyclopropyl, trifluoromethyl, trifluoroethyl, difluoromethoxy, trifluoromethoxy, difluoromethylthio or trifluoromethylthio.

$R^5$ further particularly preferably stands for —CH=CH—CH=CH— possibly substituted once or twice by fluorine, chlorine, bromine, methyl, ethyl, n- or iso-propyl, n-, iso-, sec- or tert-butyl or trifluoromethyl, if two $R^5$ moieties are in ortho position to each other.

$R^5$ quite particularly preferably stands for fluorine, chlorine, bromine, methyl, iso-propyl, tert-butyl, methoxy, iso-propoxy, methylthio, iso-propylthio, methoxymethyl, methylthiomethyl, methylamino, dimethylamino, methylaminocarbonyl, methylcarbonylamino, cyclopropyl, trifluoromethyl, trifluoroethyl, difluoromethoxy, trifluoromethoxy, difluoromethylthio or trifluoromethylthio.

$R^5$ especially preferably stands for fluorine, chlorine, bromine, methyl, trifluoromethyl, difluoromethoxy or trifluoromethoxy.

n preferably stands for 2, 3 or 4, whereby the $R^5$ moieties can be the same or different.

n particularly preferably stands for 2 or 3, whereby the $R^5$ moieties can be the same or different.

n quite particularly preferably stands for 2, particularly in the 3',4'-position, 2',4'-position, 3',5'-position, 2',3'-position or 2',5'-position, whereby the $R^5$ moieties can each be the same or different.

n further quite particularly preferably stands for 3, particularly in the 2',4',6'-position or 3',4',5'-position, whereby the $R^5$ moieties can be the same or different.

$R^6$ preferably stands for hydrogen, $C_1$-$C_6$-alkyl, $C_1$-$C_4$-alkoxy, $C_1$-$C_3$-alkoxy-$C_1$-$C_3$-alkyl, $C_3$-$C_6$-cycloalkyl; $C_1$-$C_4$-halogenalkyl, $C_1$-$C_4$-halogenalkoxy, halogen-$C_1$-$C_3$-alkoxy-$C_1$-$C_3$-alkyl, $C_3$-$C_6$-halogencycloalkyl, each with 1 to 9 fluorine, chlorine and/or bromine atoms.

$R^6$ particularly preferably stands for hydrogen, methyl, ethyl, n- or iso-propyl, tert-butyl, methoxy, ethoxy, n- or iso-propoxy, tert-butoxy, methoxymethyl, cyclopropyl; trifluoromethyl, trifluoromethoxy.

$R^7$ and $R^8$, independently of one another, preferably stand for hydrogen, $C_1$-$C_6$-alkyl, $C_1$-$C_3$-alkoxy-$C_1$-$C_3$-alkyl, $C_3$-$C_6$-cycloalkyl; $C_1$-$C_4$-halogenalkyl, halogen-$C_1$-$C_3$-alkoxy-$C_1$-$C_3$-alkyl, $C_3$-$C_6$-halogencycloalkyl, each with 1 to 9 fluorine, chlorine and/or bromine atoms.

$R^7$ and $R^8$ further preferably form, together with the nitrogen atom to which they are bonded, a saturated heterocycle with 5 or 6 ring atoms possibly substituted one to four times identically or variously by halogen or $C_1$-$C_4$-alkyl, in which the heterocycle can contain 1 or 2 additional, non-adjacent heteroatoms from the group of oxygen, sulphur or N$R^{11}$.

$R^7$ and $R^8$, independently of one another, particularly preferably stand for hydrogen, methyl, ethyl, n- or iso-propyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

$R^7$ and $R^8$ further particularly preferably form, together with the nitrogen atom to which they are bonded, a saturated heterocycle from the group of morpholine, thiomorpholine or piperazine possibly substituted one to four times, identically or variously, by fluorine, chlorine, bromine or methyl, in which the piperazine can be substituted by $R^{11}$ on the second nitrogen atom.

$R^9$ and $R^{10}$, independently of one another, preferably stand for hydrogen, $C_1$-$C_6$-alkyl, $C_3$-$C_6$-cycloalkyl; $C_1$-$C_4$-halogenalkyl, $C_3$-$C_6$-halogencycloalkyl, each with 1 to 9 fluorine, chlorine and/or bromine atoms.

$R^9$ and $R^{10}$ further preferably form, together with the nitrogen atom to which they are bonded, a saturated heterocycle with 5 or 6 ring atoms possibly substituted one to four times, identically or variously, by halogen or $C_1$-$C_4$-alkyl, in which the heterocycle can contain 1 or 2 additional, non-adjacent heteroatoms from the group of oxygen, sulphur or $NR^{11}$.

$R^9$ and $R^{10}$, independently of one another, particularly preferably stand for hydrogen, methyl, ethyl, n- or iso-propyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

$R^9$ and $R^{10}$ further particularly preferably form, together with the nitrogen atom to which they are bonded, a saturated heterocycle from the group of morpholine, thiomorpholine or piperazine possibly substituted one to four times, identically or variously, by fluorine, chlorine, bromine or methyl, in which the piperazine can be substituted by $R^{11}$ on the second nitrogen atom.

$R^{11}$ preferably stands for hydrogen or $C_1$-$C_4$-alkyl.

$R^{11}$ particularly preferably stands for hydrogen, methyl, ethyl, n- or iso-propyl, n-, iso-, sec- or tert-butyl.

Those compounds of Formula (I) are preferred, in which all moieties respectively have the abovementioned preferred definitions.

Those compounds of Formula (I) are particularly preferred, in which all moieties respectively have the abovementioned particularly preferred definitions.

Those compounds of Formula (I) are quite particularly preferred, in which all moieties respectively have the abovementioned quite particularly preferred definitions.

The following groups of novel carboxamides are preferred and are to be understood as respective subsets of the abovementioned compounds of Formula (I):

Group 1: Biphenyl Thiazole Carboxamides of Formula (I-a)

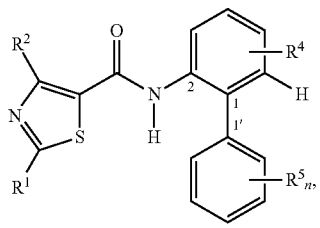

(I-a)

where $R^1$, $R^2$, $R^4$, $R^5$ and n have the meanings specified above.

Group 2: Biphenyl Thiazole Carboxamides of Formula (I-b)

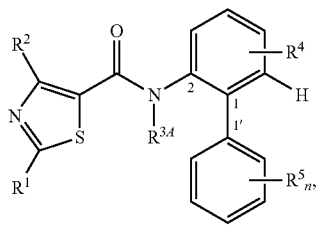

(I-b)

where $R^1$, $R^2$, $R^{3A}$, $R^4$, $R^5$ and n have the meanings specified above.

$R^{3A}$ preferably stands for $C_1$-$C_6$-alkyl, $C_1$-$C_4$-alkylsulphinyl, $C_1$-$C_4$-alkylsulphonyl, $C_1$-$C_3$-alkoxy-$C_1$-$C_3$-alkyl, $C_3$-$C_6$-cycloalkyl; $C_1$-$C_4$-halogenalkyl, $C_1$-$C_4$-halogenalkylthio, $C_1$-$C_4$-halogenalkylsulphinyl, $C_1$-$C_4$-halogenalkylsulphonyl, halogen-$C_1$-$C_3$-alkoxy-$C_1$-$C_3$-alkyl, $C_3$-$C_8$-halogencycloalkyl, each with 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halogen-($C_1$-$C_3$-alkyl)carbonyl-$C_1$-$C_3$-alkyl, halogen-($C_1$-$C_3$-alkoxy)carbonyl-$C_1$-$C_3$-alkyl, each with 1 to 13 fluorine, chlorine and/or bromine atoms; ($C_1$-$C_6$-alkyl)carbonyl, ($C_1$-$C_4$-alkoxy)carbonyl, ($C_1$-$C_3$-alkoxy-$C_1$-$C_3$-alkyl)carbonyl, ($C_3$-$C_6$-cycloalkyl)carbonyl; ($C_1$-$C_4$-halogenalkyl)carbonyl, ($C_1$-$C_4$-halogenalkoxy)carbonyl, (halogen-$C_1$-$C_3$-alkoxy-$C_1$-$C_3$-alkyl)carbonyl, ($C_3$-$C_6$-halogencycloalkyl)carbonyl, each with 1 to 9 fluorine, chlorine and/or bromine atoms; or —C(=O)C(=O)$R^6$, —CONR$^7$R$^8$ or —CH$_2$NR$^9$R$^{10}$.

$R^{3A}$ particularly preferably stands for methyl, ethyl, n- or iso-propyl, n-, iso-, sec- or tert-butyl, pentyl or hexyl, methylsulphinyl, ethylsulphinyl, n- or iso-propylsulphinyl, n-, iso-, sec- or tert-butylsulphinyl, methylsulphonyl, ethylsulphonyl, n- or iso-propylsulphonyl, n-, iso-, sec- or tert-butylsulphonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulphinyl, trifluoromethylsulphonyl, trifluoromethoxymethyl; formyl, —CH$_2$—CHO, —(CH$_2$)$_2$—CHO, —CH$_2$—CO—CH$_3$, —CH$_2$—CO—CH$_3$, —CH$_2$—CO—CH$_2$CH$_3$, —CH$_2$—CO—CH(CH$_3$)$_2$, —(CH$_2$)$_2$—CO—CH$_3$, —(CH$_2$)$_2$—CO—CH$_2$CH$_3$, —(CH$_2$)$_2$—CO—CH(CH$_3$)$_2$, —CH$_2$—CO$_2$CH$_3$, —CH$_2$—CO$_2$CH$_2$CH$_3$, —CH$_2$—CO$_2$CH(CH$_3$)$_2$, —(CH$_2$)$_2$—CO$_2$CH$_3$, —(CH$_2$)$_2$—CO$_2$CH$_2$CH$_3$, —(CH$_2$)$_2$—CO$_2$CH(CH$_3$)$_2$, —CH$_2$—CO—CF$_3$, —CH$_2$—CO—CCl$_3$, —CH$_2$—CO—CH$_2$CF$_3$, —CH$_2$—CO—CH$_2$CCl$_3$, —(CH$_2$)$_2$—CO—CH$_2$CF$_3$, —(CH$_2$)$_2$—CO—CH$_2$CCl$_3$, —CH$_2$—CO$_2$CH$_2$CF$_3$, —CH$_2$—CO$_2$CF$_2$CF$_3$, —CH$_2$—CO$_2$CH$_2$CCl$_3$, —CH$_2$—CO$_2$CCl$_2$CCl$_3$, —(CH$_2$)$_2$—CO$_2$CH$_2$CF$_3$, —(CH$_2$)$_2$—CO$_2$CF$_2$CF$_3$, —(CH$_2$)$_2$—CO$_2$CH$_2$CCl$_3$, —(CH$_2$)$_2$—CO$_2$CCl$_2$CCl$_3$; methyl carbonyl, ethyl carbonyl, n-propylcarbonyl, iso-propylcarbonyl, tert-butylcarbonyl, methoxycarbonyl, ethoxycarbonyl, tert-butoxycarbonyl, cyclopropylcarbonyl; trifluoromethylcarbonyl, trifluoromethoxycarbonyl, or —C(=O)C(=O)$R^6$, —CONR$^7$R$^8$ or —CH$_2$NR$^9$R$^{10}$.

$R^{3A}$ quite particularly preferably stands for methyl, methoxymethyl, formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —C(=O)CHO, —C(=O)C(=O)CH$_3$, —C(=O)C(=O)CH$_2$OCH$_3$, —C(=O)CO$_2$CH$_3$, —C(=O)CO$_2$CH$_2$CH$_3$.

Group 3: Biphenyl Thiazole Carboxamides of Formula (I-c)

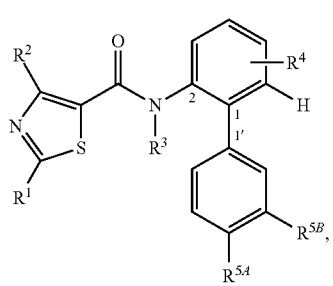

(I-c)

where $R^1$, $R^2$, $R^3$ and $R^4$ have the meanings specified above and $R^{5A}$ and $R^{5B}$ have the meanings of $R^5$ independently of one another.

Group 4: Biphenyl Thiazole Carboxamides of Formula (I-d)

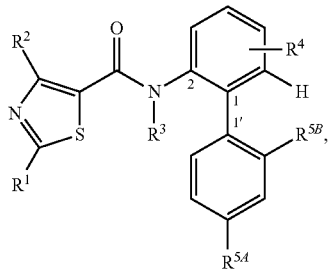

(I-d)

where $R^1$, $R^2$, $R^3$ and $R^4$ have the meanings specified above and $R^{5A}$ and $R^{5B}$ have the meanings of $R^5$ independently of one another.

Group 5: Biphenyl Thiazole Carboxamides of Formula (I-e)

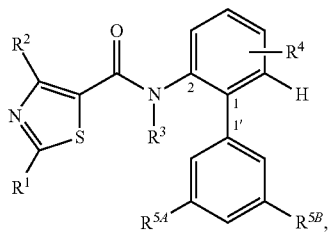

(I-e)

where $R^1$, $R^2$, $R^3$ and $R^4$ have the meanings specified above and $R^{5A}$ and $R^{5B}$ have the meanings of $R^5$ independently of one another.

Group 6: Biphenyl Thiazole Carboxamides of Formula (I-f)

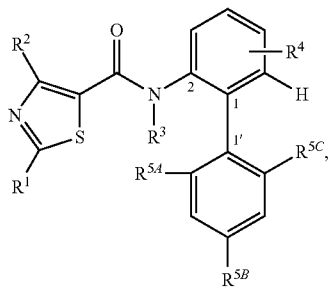

(I-f)

where $R^1$, $R^2$, $R^3$ and $R^4$ have the meanings specified above and $R^{5A}$ and $R^{5B}$ and $R^{5C}$ have the meanings of $R^5$ independently of one another.

Group 7: Biphenyl Thiazole Carboxamides of Formula (I-g)

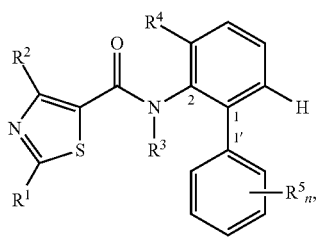

(I-g)

where $R^1$, $R^2$, $R^3$, $R^4$, $R^5$ and n have the meanings specified above.

Group 8: Biphenyl Thiazole Carboxamides of Formula (I-h)

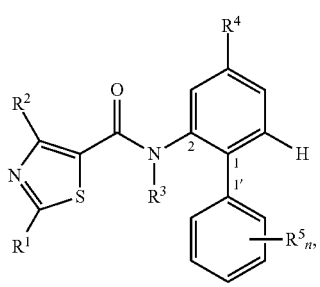

(I-h)

where $R^1$, $R^2$, $R^3$, $R^4$, $R^5$ and n have the meanings specified above.

Group 9: Biphenyl Thiazole Carboxamides of Formula (I-i)

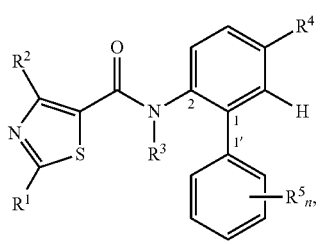

(I-i)

where $R^1$, $R^2$, $R^3$, $R^4$, $R^5$ and n have the meanings specified above.

Group 10: Biphenyl Thiazole Carboxamides of Formula (I-j)

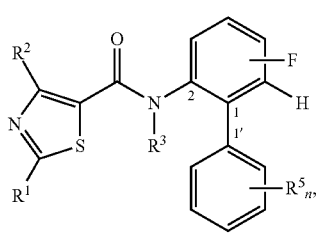

(I-j)

where $R^1$, $R^2$, $R^3$, $R^5$ and n have the meanings specified above.

Group 11: Biphenyl Thiazole Carboxamides of Formula (I-k)

(I-k)

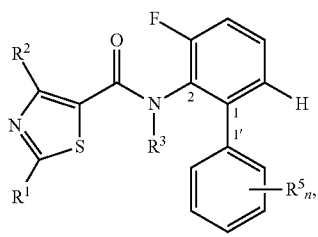

where $R^1$, $R^2$, $R^3$, $R^5$ and n have the meanings specified above.

Group 12: Biphenyl Thiazole Carboxamides of Formula (I-l)

(I-l)

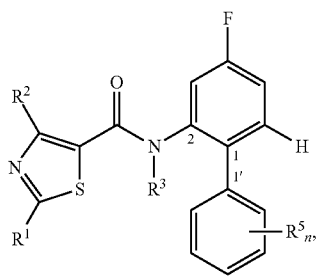

where $R^1$, $R^2$, $R^3$, $R^5$ and n have the meanings specified above.

Group 13: Biphenyl Thiazole Carboxamides of Formula (I-m)

(I-m)

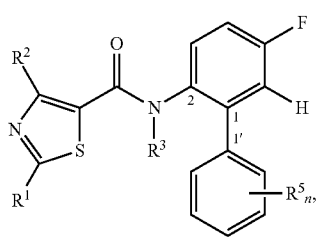

where $R^1$, $R^2$, $R^3$, $R^5$ and n have the meanings specified above.

Group 14: Biphenyl Thiazole Carboxamides of Formula (I-n)

(I-n)

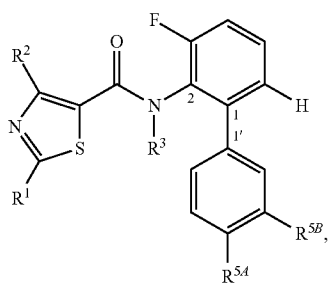

where $R^1$, $R^2$, $R^3$ and $R^4$ have the meanings specified above and $R^{5A}$ and $R^{5B}$ have the meanings of $R^5$ independently of one another.

Group 15: Biphenyl Thiazole Carboxamides of Formula (I-o)

(I-o)

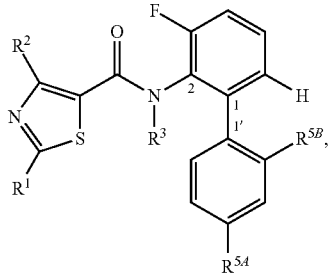

where $R^1$, $R^2$, $R^3$ and $R^4$ have the meanings specified above and $R^{5A}$ and $R^{5B}$ have the meanings of $R^5$ independently of one another.

Group 16: Biphenyl Thiazole Carboxamides of Formula (I-p)

(I-p)

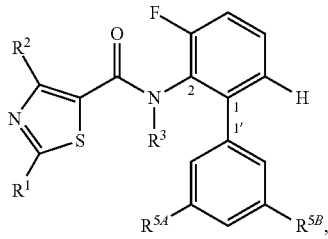

where $R^1$, $R^2$, $R^3$ and $R^4$ have the meanings specified above and $R^{5A}$ and $R^{5B}$ have the meanings of $R^5$ independently of one another.

Group 17: Biphenyl Thiazole Carboxamides of Formula (I-q)

(I-q)

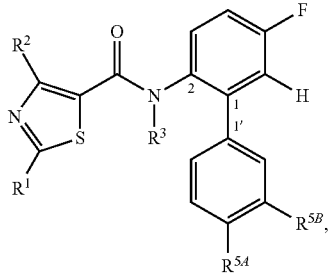

where $R^1$, $R^2$, $R^3$ and $R^4$ have the meanings specified above and $R^{5A}$ and $R^{5B}$ have the meanings of $R^5$ independently of one another.

Group 18: Biphenyl Thiazole Carboxamides of Formula (I-r)

(I-r)

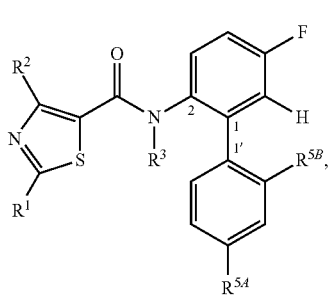

where $R^1$, $R^2$, $R^3$ and $R^4$ have the meanings specified above and $R^{5A}$ and $R^{5B}$ have the meanings of $R^5$ independently of one another.

Group 19: Biphenyl Thiazole Carboxamides of Formula (I-s)

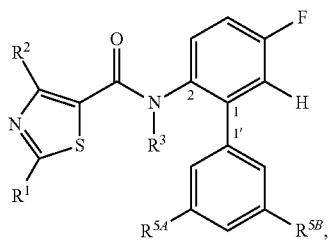

(I-s)

where $R^1$, $R^2$, $R^3$ and $R^4$ have the meanings specified above and $R^{5A}$ and $R^{5B}$ have the meanings of $R^5$ independently of one another.

Compounds of Formula (I) are emphasised (as are Groups 1 to 19), in which $R^1$ stands for methyl.

Compounds of Formula (I) are emphasised (as are Groups 1 to 19), in which $R^2$ stands for difluoromethyl or trifluoromethyl.

Compounds of Formula (I) are emphasised (as are Groups 1 to 9), in which $R^4$ stands for chlorine, bromine, $C_1$-$C_4$-alkyl, $C_1$-$C_4$-alkoxy, $C_1$-$C_4$-alkylthio or $C_1$-$C_4$-halogenalkyl with 1 to 9 fluorine, chlorine and/or bromine atoms.

Compounds of Formula (I) are emphasised (as are Groups 1 to 9), in which $R^4$ stands for chlorine, methyl, trifluoromethyl, methoxy or methylthio, and especially for chlorine.

Compounds of Formula (I) are emphasised (as are Groups 1 to 19), in which $R^3$ stands for formyl. Furthermore, compounds of Formula (I) are emphasised (as are Groups 1 to 19), in which $R^3$ stands for —C(=O)C(=O)$R^6$, where $R^6$ has the meanings specified above.

Examples for the compounds of Formulae (I-j) to (I-s) are given in Table 1 below:

TABLE 1

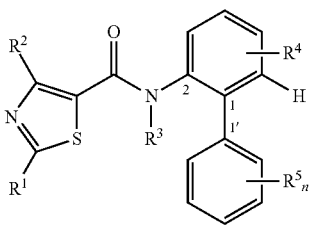

| No. | $R^1$ | $R^2$ | $R^3$ | $R^4$ | $R^5$ |
|---|---|---|---|---|---|
| 1.01 | $CH_3$ | $CF_3$ | H | 3-F | 3',4'-$Cl_2$ |
| 1.02 | $CH_3$ | $CF_3$ | H | 3-F | 3',4'-$F_2$ |
| 1.03 | $CH_3$ | $CF_3$ | H | 3-F | 2',4'-$Cl_2$ |
| 1.04 | $CH_3$ | $CF_3$ | H | 3-F | 2',4'-$F_2$ |
| 1.05 | $CH_3$ | $CF_3$ | H | 3-F | 3'-F, 4'-Cl |
| 1.06 | $CH_3$ | $CF_3$ | H | 3-F | '3-Cl, 4'-F |
| 1.07 | $CH_3$ | $CF_3$ | H | 3-F | 3'-$CH_3$, 4'-Cl |
| 1.08 | $CH_3$ | $CF_3$ | H | 3-F | 3'-$CH_3$, 4'-F |
| 1.09 | $CH_3$ | $CF_3$ | H | 3-F | 3',5'-$Cl_2$ |
| 1.10 | $CH_3$ | $CF_3$ | H | 3-F | 3',5'-$(CH_3)_2$ |
| 1.11 | $CH_3$ | $CF_3$ | H | 3-F | 3',5'-$(CF_3)_2$ |
| 1.12 | $CH_3$ | $CF_3$ | H | 3-F | 3',5'-$F_2$ |
| 1.13 | $CH_3$ | $CF_3$ | H | 3-F | 2',5'-$Cl_2$ |
| 1.14 | $CH_3$ | $CF_3$ | H | 3-F | 2',5'-$F_2$ |
| 1.15 | $CH_3$ | $CF_3$ | H | 3-F | 2'-F, 3'-Cl |
| 1.16 | $CH_3$ | $CF_3$ | H | 5-F | 3',4'-$Cl_2$ |

TABLE 1-continued

| No. | $R^1$ | $R^2$ | $R^3$ | $R^4$ | $R^5$ |
|---|---|---|---|---|---|
| 1.17 | $CH_3$ | $CF_3$ | H | 5-F | 3',4'-$F_2$ |
| 1.18 | $CH_3$ | $CF_3$ | H | 5-F | 2',4'-$Cl_2$ |
| 1.19 | $CH_3$ | $CF_3$ | H | 5-F | 2',4'-$F_2$ |
| 1.20 | $CH_3$ | $CF_3$ | H | 5-F | 3'-F, 4'-Cl |
| 1.21 | $CH_3$ | $CF_3$ | H | 5-F | '3-Cl, 4'-F |
| 1.22 | $CH_3$ | $CF_3$ | H | 5-F | 3'-$CH_3$, 4'-Cl |
| 1.23 | $CH_3$ | $CF_3$ | H | 5-F | 3'-$CH_3$, 4'-F |
| 1.24 | $CH_3$ | $CF_3$ | H | 5-F | 3',5'-$Cl_2$ |
| 1.25 | $CH_3$ | $CF_3$ | H | 5-F | 3',5'-$(CH_3)_2$ |
| 1.26 | $CH_3$ | $CF_3$ | H | 5-F | 3',5'-$(CF_3)_2$ |
| 1.27 | $CH_3$ | $CF_3$ | H | 5-F | 3',5'-$F_2$ |
| 1.28 | $CH_3$ | $CF_3$ | H | 5-F | 2',5'-$Cl_2$ |
| 1.29 | $CH_3$ | $CF_3$ | H | 5-F | 2',5'-$F_2$ |
| 1.30 | $CH_3$ | $CF_3$ | H | 5-F | 2'-F, 3'-Cl |
| 1.31 | $CH_3$ | $CHF_2$ | H | 3-F | 3',4'-$Cl_2$ |
| 1.32 | $CH_3$ | $CHF_2$ | H | 3-F | 3',4'-$F_2$ |
| 1.33 | $CH_3$ | $CHF_2$ | H | 3-F | 2',4'-$Cl_2$ |
| 1.34 | $CH_3$ | $CHF_2$ | H | 3-F | 2',4'-$F_2$ |
| 1.35 | $CH_3$ | $CHF_2$ | H | 3-F | 3'-F, 4'-Cl |
| 1.36 | $CH_3$ | $CHF_2$ | H | 3-F | '3-Cl, 4'-F |
| 1.37 | $CH_3$ | $CHF_2$ | H | 3-F | 3'-$CH_3$, 4'-Cl |
| 1.38 | $CH_3$ | $CHF_2$ | H | 3-F | 3'-$CH_3$, 4'-F |
| 1.39 | $CH_3$ | $CHF_2$ | H | 3-F | 3',5'-$Cl_2$ |
| 1.40 | $CH_3$ | $CHF_2$ | H | 3-F | 3',5'-$(CH_3)_2$ |
| 1.41 | $CH_3$ | $CHF_2$ | H | 3-F | 3',5'-$(CF_3)_2$ |
| 1.42 | $CH_3$ | $CHF_2$ | H | 3-F | 3',5'-$F_2$ |
| 1.43 | $CH_3$ | $CHF_2$ | H | 3-F | 2',5'-$Cl_2$ |
| 1.44 | $CH_3$ | $CHF_2$ | H | 3-F | 2',5'-$F_2$ |
| 1.45 | $CH_3$ | $CHF_2$ | H | 3-F | 2'-F, 3'-Cl |
| 1.46 | $CH_3$ | $CHF_2$ | H | 5-F | 3',4'-$Cl_2$ |
| 1.47 | $CH_3$ | $CHF_2$ | H | 5-F | 3',4'-$F_2$ |
| 1.48 | $CH_3$ | $CHF_2$ | H | 5-F | 2',4'-$Cl_2$ |
| 1.49 | $CH_3$ | $CHF_2$ | H | 5-F | 2',4'-$F_2$ |
| 1.50 | $CH_3$ | $CHF_2$ | H | 5-F | 3'-F, 4'-Cl |
| 1.51 | $CH_3$ | $CHF_2$ | H | 5-F | '3-Cl, 4'-F |
| 1.52 | $CH_3$ | $CHF_2$ | H | 5-F | 3'-$CH_3$, 4'-Cl |
| 1.53 | $CH_3$ | $CHF_2$ | H | 5-F | 3'-$CH_3$, 4'-F |
| 1.54 | $CH_3$ | $CHF_2$ | H | 5-F | 3',5'-$Cl_2$ |
| 1.55 | $CH_3$ | $CHF_2$ | H | 5-F | 3',5'-$(CH_3)_2$ |
| 1.56 | $CH_3$ | $CHF_2$ | H | 5-F | 3',5'-$(CF_3)_2$ |
| 1.57 | $CH_3$ | $CHF_2$ | H | 5-F | 3',5'-$F_2$ |
| 1.58 | $CH_3$ | $CHF_2$ | H | 5-F | 2',5'-$Cl_2$ |
| 1.59 | $CH_3$ | $CHF_2$ | H | 5-F | 2',5'-$F_2$ |
| 1.60 | $CH_3$ | $CHF_2$ | H | 5-F | 2'-F, 3'-Cl |
| 1.61 | $N(CH_3)_2$ | $CF_3$ | H | 3-F | 3',4'-$Cl_2$ |
| 1.62 | $N(CH_3)_2$ | $CF_3$ | H | 3-F | 3',4'-$F_2$ |
| 1.63 | $N(CH_3)_2$ | $CF_3$ | H | 3-F | 2',4'-$Cl_2$ |
| 1.64 | $N(CH_3)_2$ | $CF_3$ | H | 3-F | 2',4'-$F_2$ |
| 1.65 | $N(CH_3)_2$ | $CF_3$ | H | 3-F | 3'-F, 4'-Cl |
| 1.66 | $N(CH_3)_2$ | $CF_3$ | H | 3-F | '3-Cl, 4'-F |
| 1.67 | $N(CH_3)_2$ | $CF_3$ | H | 3-F | 3'-$CH_3$, 4'-Cl |
| 1.68 | $N(CH_3)_2$ | $CF_3$ | H | 3-F | 3'-$CH_3$, 4'-F |
| 1.69 | $N(CH_3)_2$ | $CF_3$ | H | 3-F | 3',5'-$Cl_2$ |
| 1.70 | $N(CH_3)_2$ | $CF_3$ | H | 3-F | 3',5'-$(CH_3)_2$ |
| 1.71 | $N(CH_3)_2$ | $CF_3$ | H | 3-F | 3',5'-$(CF_3)_2$ |
| 1.72 | $N(CH_3)_2$ | $CF_3$ | H | 3-F | 3',5'-$F_2$ |
| 1.73 | $N(CH_3)_2$ | $CF_3$ | H | 3-F | 2',5'-$Cl_2$ |
| 1.74 | $N(CH_3)_2$ | $CF_3$ | H | 3-F | 2',5'-$F_2$ |
| 1.75 | $N(CH_3)_2$ | $CF_3$ | H | 3-F | 2'-F, 3'-Cl |
| 1.76 | $N(CH_3)_2$ | $CF_3$ | H | 5-F | 3',4'-$Cl_2$ |
| 1.77 | $N(CH_3)_2$ | $CF_3$ | H | 5-F | 3',4'-$F_2$ |
| 1.78 | $N(CH_3)_2$ | $CF_3$ | H | 5-F | 2',4'-$Cl_2$ |
| 1.79 | $N(CH_3)_2$ | $CF_3$ | H | 5-F | 2',4'-$F_2$ |
| 1.80 | $N(CH_3)_2$ | $CF_3$ | H | 5-F | 3'-F, 4'-Cl |
| 1.81 | $N(CH_3)_2$ | $CF_3$ | H | 5-F | '3-Cl, 4'-F |
| 1.82 | $N(CH_3)_2$ | $CF_3$ | H | 5-F | 3'-$CH_3$, 4'-Cl |

TABLE 1-continued

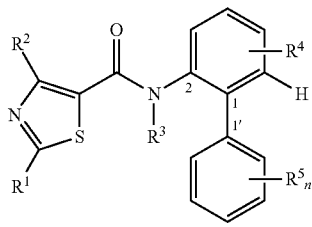

| No. | R¹ | R² | R³ | R⁴ | R⁵ |
|---|---|---|---|---|---|
| 1.83 | $N(CH_3)_2$ | $CF_3$ | H | 5-F | 3'-$CH_3$, 4'-F |
| 1.84 | $N(CH_3)_2$ | $CF_3$ | H | 5-F | 3',5'-$Cl_2$ |
| 1.85 | $N(CH_3)_2$ | $CF_3$ | H | 5-F | 3',5'-$(CH_3)_2$ |
| 1.86 | $N(CH_3)_2$ | $CF_3$ | H | 5-F | 3',5'-$(CF_3)_2$ |
| 1.87 | $N(CH_3)_2$ | $CF_3$ | H | 5-F | 3',5'-$F_2$ |
| 1.88 | $N(CH_3)_2$ | $CF_3$ | H | 5-F | 2',5'-$Cl_2$ |
| 1.89 | $N(CH_3)_2$ | $CF_3$ | H | 5-F | 2',5'-$F_2$ |
| 1.90 | $N(CH_3)_2$ | $CF_3$ | H | 5-F | 2'-F, 3'-Cl |
| 1.91 | $N(CH_3)_2$ | $CHF_2$ | H | 3-F | 3',4'-$Cl_2$ |
| 1.92 | $N(CH_3)_2$ | $CHF_2$ | H | 3-F | 3',4'-$F_2$ |
| 1.93 | $N(CH_3)_2$ | $CHF_2$ | H | 3-F | 2',4'-$Cl_2$ |
| 1.94 | $N(CH_3)_2$ | $CHF_2$ | H | 3-F | 2',4'-$F_2$ |
| 1.95 | $N(CH_3)_2$ | $CHF_2$ | H | 3-F | 3'-F, 4'-Cl |
| 1.96 | $N(CH_3)_2$ | $CHF_2$ | H | 3-F | '3-Cl, 4'-F |
| 1.97 | $N(CH_3)_2$ | $CHF_2$ | H | 3-F | 3'-$CH_3$, 4'-Cl |
| 1.98 | $N(CH_3)_2$ | $CHF_2$ | H | 3-F | 3'-$CH_3$, 4'-F |
| 1.99 | $N(CH_3)_2$ | $CHF_2$ | H | 3-F | 3',5'-$Cl_2$ |
| 1.100 | $N(CH_3)_2$ | $CHF_2$ | H | 3-F | 3',5'-$(CH_3)_2$ |
| 1.101 | $N(CH_3)_2$ | $CHF_2$ | H | 3-F | 3',5'-$(CF_3)_2$ |
| 1.102 | $N(CH_3)_2$ | $CHF_2$ | H | 3-F | 3',5'-$F_2$ |
| 1.103 | $N(CH_3)_2$ | $CHF_2$ | H | 3-F | 2',5'-$Cl_2$ |
| 1.104 | $N(CH_3)_2$ | $CHF_2$ | H | 3-F | 2',5'-$F_2$ |
| 1.105 | $N(CH_3)_2$ | $CHF_2$ | H | 3-F | 2'-F, 3'-Cl |
| 1.106 | $N(CH_3)_2$ | $CHF_2$ | H | 5-F | 3',4'-$Cl_2$ |
| 1.107 | $N(CH_3)_2$ | $CHF_2$ | H | 5-F | 3',4'-$F_2$ |
| 1.108 | $N(CH_3)_2$ | $CHF_2$ | H | 5-F | 2',4'-$Cl_2$ |
| 1.109 | $N(CH_3)_2$ | $CHF_2$ | H | 5-F | 2',4'-$F_2$ |
| 1.110 | $N(CH_3)_2$ | $CHF_2$ | H | 5-F | 3'-F, 4'-Cl |
| 1.111 | $N(CH_3)_2$ | $CHF_2$ | H | 5-F | '3-Cl, 4'-F |
| 1.112 | $N(CH_3)_2$ | $CHF_2$ | H | 5-F | 3'-$CH_3$, 4'-Cl |
| 1.113 | $N(CH_3)_2$ | $CHF_2$ | H | 5-F | 3'-$CH_3$, 4'-F |
| 1.114 | $N(CH_3)_2$ | $CHF_2$ | H | 5-F | 3',5'-$Cl_2$ |
| 1.115 | $N(CH_3)_2$ | $CHF_2$ | H | 5-F | 3',5'-$(CH_3)_2$ |
| 1.116 | $N(CH_3)_2$ | $CHF_2$ | H | 5-F | 3',5'-$(CF_3)_2$ |
| 1.117 | $N(CH_3)_2$ | $CHF_2$ | H | 5-F | 3',5'-$F_2$ |
| 1.118 | $N(CH_3)_2$ | $CHF_2$ | H | 5-F | 2',5'-$Cl_2$ |
| 1.119 | $N(CH_3)_2$ | $CHF_2$ | H | 5-F | 2',5'-$F_2$ |
| 1.120 | $N(CH_3)_2$ | $CHF_2$ | H | 5-F | 2'-F, 3'-Cl |

Saturated or unsaturated hydrocarbon moieties such as alkyl or alkenyl can be straight-chained or branched, respectively, including in combination with heteroatoms such as e.g. in alkoxy, if possible.

Possibly substituted moieties can be substituted once or several times, and if substituted several times, the substituents can be the same or different. Thus, the definition for dialkylamino also includes an amino group asymmetrically substituted by alkyl such as, for example, methylethylamino.

Moieties substituted with halogen such as e.g. halogenalkyl can be halogenated once or several times. If halogenated several times, the halogen atoms can be the same or different. In this case, halogen stands for fluorine, chlorine, bromine and iodine, particularly for fluorine, chlorine and bromine.

The general definitions and the preferred moiety definitions and explanations indicated above can be combined in any manner among the respective groups and preferred groups. They are valid for the final products, preliminary products and intermediate products. In particular, the compounds named in Groups 1 to 6 can be combined with the general, preferred, particularly preferred, etc. definitions, whereby all respective combinations among the preferred definitions are possible as well.

Description of the Methods According to the Invention for the Preparation of the Biphenyl Thiazole Carboxamides of Formula (I) as Well as the Intermediate Products Method (a)

If 2-methyl-4-(trifluoromethyl)-1,3-thiazole-5-carbonylchloride and 4'-chloro-3',5-difluorobiphenyl-2-amine are used as initial substances, Method (a) according to the invention can be illustrated by the following reaction diagram:

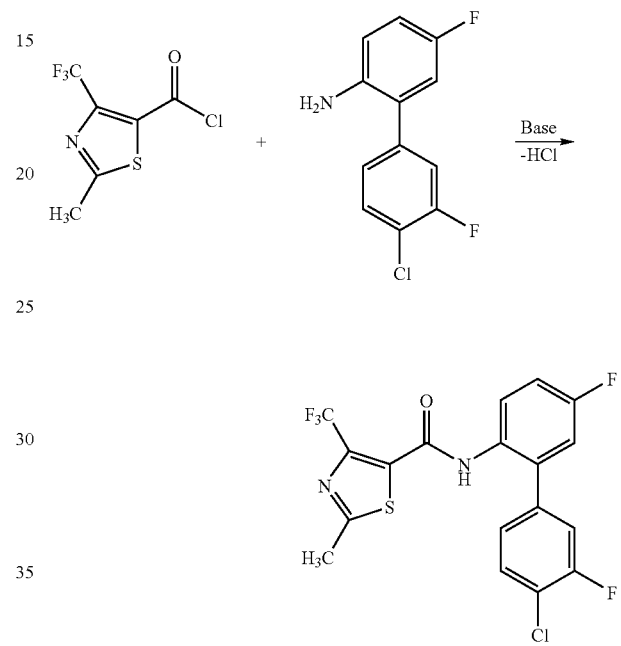

The carboxylic acid derivatives, which are necessary as initial substances for carrying out Method (a) according to the invention, are generally defined by Formula (II). In Formula (II), R¹ and R² preferably, particularly preferably and quite particularly preferably stand for those meanings that were already indicated for these moieties as preferred, particularly preferred and quite particularly preferred in reference to the description of the compounds of Formula (I) according to the invention. X¹ preferably stands for chlorine, bromine or hydroxy.

The carboxylic acid derivatives of Formula (II) are known and/or can be manufactured according to known methods (see WO 03/066609, WO 03/066610, EP-A 0 545 099, EP-A 0 589 301, EP-A 0 589 313 and U.S. Pat. No. 3,547,917).

The biphenyl amines, which are further necessary as initial substances for carrying out Method (a) according to the invention, are generally defined by Formula (III). In Formula (III), R³, R⁴, R⁵ and n preferably, particularly preferably and quite particularly preferably have those meanings that were already indicated for these moieties or this index as preferred, particularly preferred and quite particularly preferred in reference to the description of compounds of Formula (I) according to the invention.

The biphenyl amines of Formula (III) are partially known or can be obtained according to known methods (see e.g. WO 03/070705, WO 97/08148, and JP 2001-302605).

It is also possible, to first manufacture biphenyl amines of Formula (III-a)

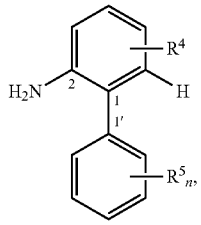

(III-a)

where $R^{3,4}$, $R^4$, $R^5$ and n have the meanings specified above, and then to react these with halogenides of Formula (VIII)

$$R^{3,4}—X^4 \qquad (VIII),$$

where $R^{3,4}$ and $X^4$ have the meanings specified above, in the presence of a base and in the presence of a diluent. [The reaction conditions of (e) according to the invention apply accordingly.]

Method (b)

If N-(2-bromo-4-fluorophenyl)-2-methyl-4-(trifluoromethyl)-1,3-thiazole-5-carboxamide and (4-chloro-3-fluorophenyl)boronic acid are used as initial substances and a catalyst is employed as well, the progression of Method (b) according to the invention can be illustrated by the following reaction diagram:

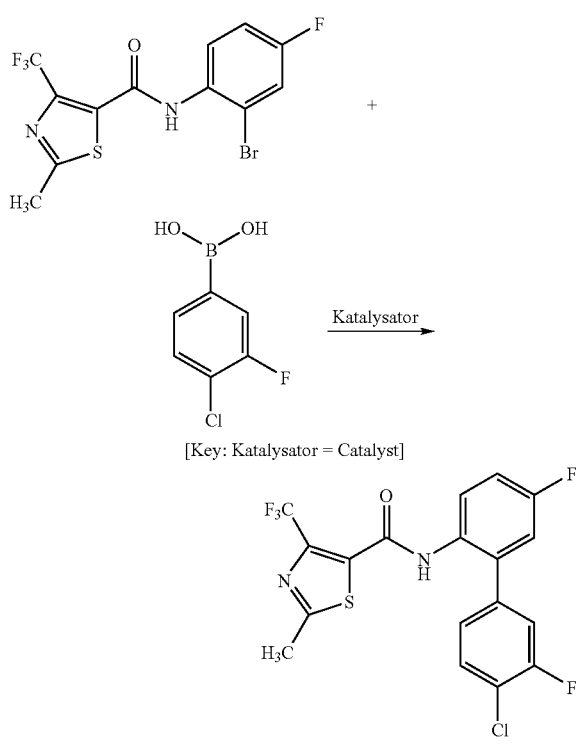

[Key: Katalysator = Catalyst]

The halogen carboxamides, which are necessary as initial substances for carrying out Method (b) according to the invention, are generally defined by Formula (IV). In Formula (IV), $R^1$, $R^2$, $R^3$ and $R^4$ preferably, particularly preferably and quite particularly preferably have those meanings that were already indicated for these moieties as preferred, particularly preferred and quite particularly preferred in reference to the description of compounds of Formula (I) according to the invention. $X^2$ stands for bromine or iodine.

The halogen carboxamides of Formula (IV) are not yet known. As novel chemical compounds, they are a further subject of the present patent application. They are obtained by reacting (f) Carboxylic Acid Derivatives of Formula (II)

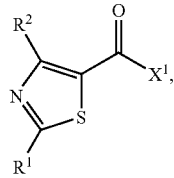

(II)

where $R^1$, Hal and $X^1$ have the meanings specified above, with halogen anilines of Formula (IX)

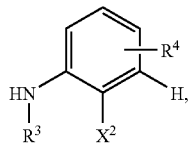

(IX)

where $R^3$, $R^4$ and $X^2$ have the meanings specified above,
in the presence of a catalyst if applicable, in the presence of a condensation agent if applicable, in the presence of an acid binding agent if applicable and in the presence of a diluent if applicable.

The carboxylic acid derivatives of Formula (II), which are necessary as initial substances for carrying out Method (f) according to the invention, were already described in reference to Method (a) according to the invention.

The halogen anilines, which are further necessary as initial substances for carrying out Method (f) according to the invention, are generally defined by Formula (IX). In Formula (IX), $R^3$, $R^4$ and $X^2$ preferably, particularly preferably and quite particularly preferably have those meanings that were already indicated for these moieties as preferred, particularly preferred and quite particularly preferred in conjunction with the description of compounds of Formula (I) according to the invention and the description of the preliminary products of Formula (IV) according to the invention.

The halogen anilines of Formula (IX) are commercially available synthesis chemicals or can be obtained according to known methods.

It is also possible to first manufacture halogen anilines of Formula (IX-a)

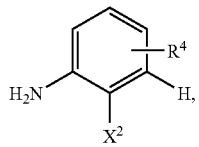

(IX-a)

where $R^4$ and $X^2$ have the meanings specified above, and subsequently react them with halogenides of Formula (VIII)

$$R^{3,4}—X^4 \qquad (VIII),$$

where $R^{3,4}$ and $X^4$ have the meanings specified above, in the presence of a base and in the presence of a diluent. [The reaction conditions of (i) according to the invention apply accordingly.]

The boronic acid derivatives, which are further necessary as initial substances for carrying out Method (b) according to the invention, are generally defined by Formula (V). In Formula (V), $R^5$ and n preferably, particularly preferably and quite particularly preferably have those meanings that were already indicated for this moiety and index as preferred, particularly preferred and quite particularly preferred in conjunction with the description of compounds of Formula (I) according to the invention. $G^1$ and $G^2$ each stand for hydrogen or together stand for tetramethylethylene.

The boronic acid derivatives of Formula (V) are known and/or can be manufactured according to known methods (see e.g. WO 01/90084, JP-A 2001-302605 and U.S. Pat. No. 5,633,218).

Method (c)

If [5-fluoro-2-({[2-methyl-4-(trifluoromethyl)-1,3-thiazole-5-yl]carbonyl}amino)phenyl]boronic acid and 4-bromo-1,2-dichlorobenzene are used as initial substances and a catalyst is employed as well, the progression of Method (c) according to the invention can be illustrated by the following reaction diagram:

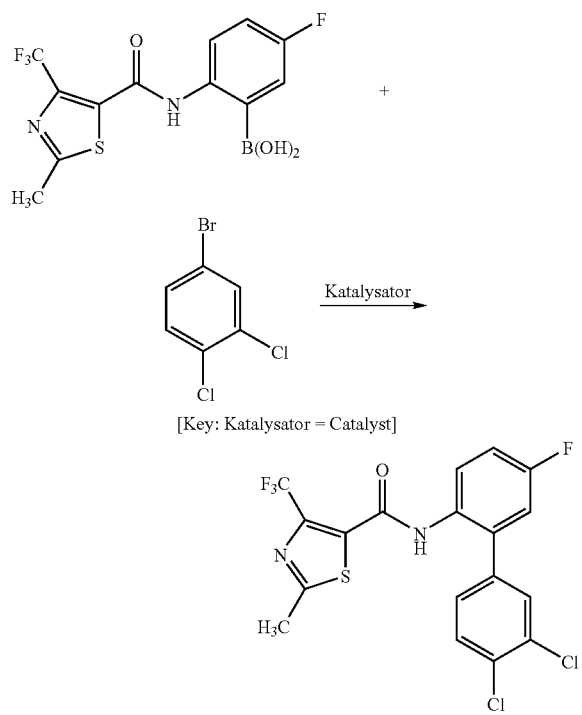

[Key: Katalysator = Catalyst]

The boronic acid derivatives, which are necessary as initial substances for carrying out Method (c) according to the invention, are generally defined by Formula (VI). In Formula (VI), $R^1$, $R^2$, $R^3$ and $R^4$ preferably, particularly preferably and quite particularly preferably have those meanings that were already indicated for these moieties as preferred, particularly preferred and quite particularly preferred in conjunction with the description of compounds of Formula (I) according to the invention. $G^3$ and $G^4$ each stand for hydrogen or jointly stand for tetramethylethylene.

The boronic acid derivatives of Formula (VI) are not yet known. As novel chemical compounds, they are a further subject of the present patent application. They are obtained by reacting (g) a Carboxylic Acid Derivative of Formula (II)

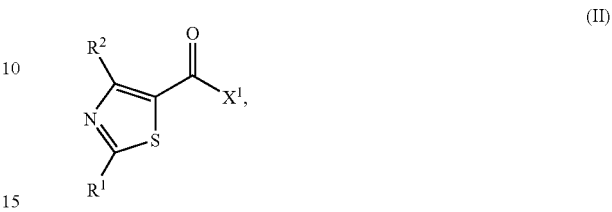

where $R^1$, $R^2$ and $X^1$ have the meanings specified above, with an aniline boronic acid derivative of Formula (X)

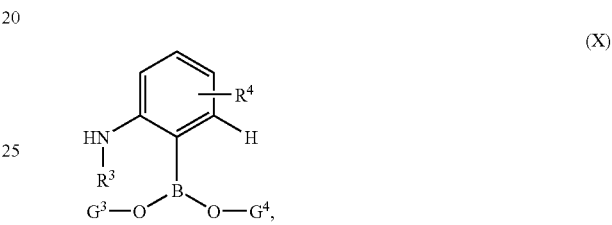

where $R^3$, $R^4$, $G^3$ and $G^4$ have the meanings specified above,
in the presence of a catalyst if applicable, in the presence of a condensation agent if applicable, in the presence of an acid binding agent if applicable and in the presence of a diluent if applicable.

The carboxylic acid derivatives of Formula (II), which are necessary as initial substances for carrying out Method (g) according to the invention, were already described in reference to Method (a) according to the invention.

The aniline boronic acid derivatives, which are additionally necessary as initial substances for carrying out Method (g) according to the invention, are generally described by Formula (X). In Formula (X), $R^3$ and $R^4$ preferably, particularly preferably and quite particularly preferably have those meanings that were already indicated for these moieties as preferred, particularly preferred and quite particularly preferred in conjunction with the description of compounds of Formula (I) according to the invention. $G^3$ and $G^4$ each stand for hydrogen or jointly stand for tetramethylethylene.

The aniline boronic acid derivatives of Formula (X) are known synthesis chemicals or can be obtained according to known methods.

It is also possible to first manufacture aniline boronic acid derivatives of Formula (X-a)

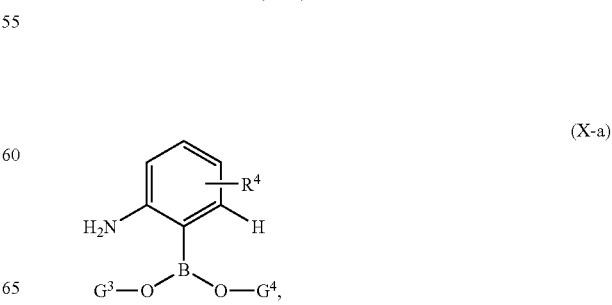

where $R^4$, $G^3$ and $G^4$ have the meanings specified above, and to subsequently react them with halogenides of Formula (VIII), $$R^{3,4}\text{—}X^4 \quad (VIII)$$

where $R^{3,4}$ and $X^4$ have the meanings specified above, in the presence of a base and in the presence of a diluent. [The reaction conditions of (i) according to the invention apply accordingly.]

The phenyl derivatives, which are further necessary as initial substances for carrying out Method (c) according to the invention, are generally defined by Formula (VII). In Formula (VII), $R^5$ and n preferably, particularly preferably and quite particularly preferably have those meanings that were already indicated for this moiety and index as preferred, particularly preferred and quite particularly preferred in conjunction with the description of compounds of Formula (I) according to the invention. $X^3$ stands for chlorine, bromine, iodine or trifluoromethylsulphonate.

The phenyl derivatives of Formula (VII) are known synthesis chemicals.

Method (d)

If N-(2-bromo-4-fluorophenyl)-2-methyl-4-(trifluoromethyl)-1,3-thiazole-5-carboxamide and 4-bromo-1,2-dichlorobenzene are used as initial substances, and a catalyst and 4,4,4',4',5,5,5',5'-octamethyl-2,2'-bis-1,3,2-dioxaborolane are employed as well, the progression of Method (d) according to the invention can be illustrated by the following reaction diagram:

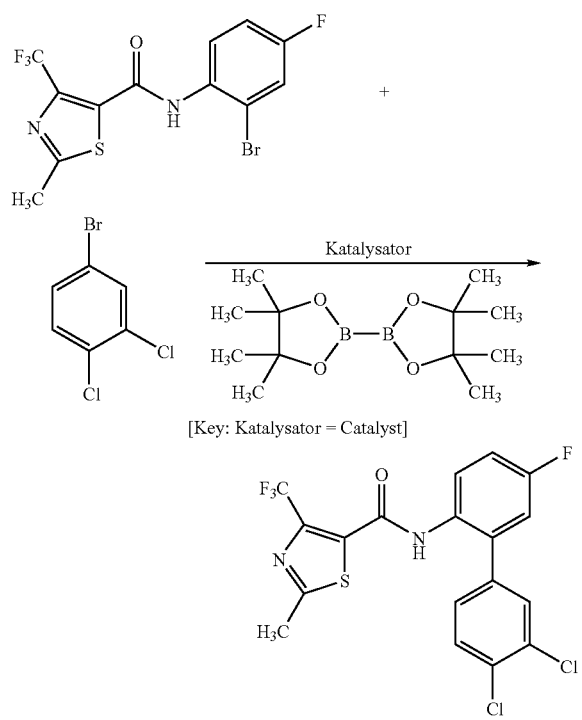

[Key: Katalysator = Catalyst]

The halogen carboxamides of Formula (IV), which are necessary as initial substances for carrying out Method (d) according to the invention, as well as the phenyl derivatives of Formula (VII), were already described in conjunction with Methods (b) and (c) according to the invention.

The 4,4,4',4',5,5,5',5'-octamethyl-2,2'-bis-1,3,2-dioxaborolane, which is further necessary for carrying out Method (d) according to the invention, is a commercially available synthesis chemical.

Method (e)

If N-(3',4'-dichloro-5-fluorobiphenyl-2-yl)-2-methyl-4-(trifluoromethyl)-1,3-thiazole-5-carboxamide and acetyl chloride are used as initial substances, the progression of Method (e) according to the invention can be illustrated by the following reaction diagram:

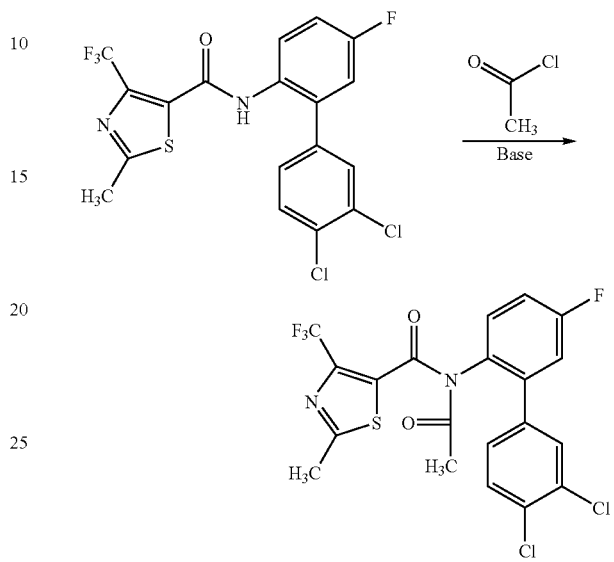

The biphenyl thiazole carboxamides, which are necessary as initial substances for carrying out Method (e) according to the invention, are generally defined by Formula (I-a). In Formula (I-a), $R^1$, $R^2$, $R^4$, $R^5$ and n preferably, particularly preferably and quite particularly preferably have those meanings that were already indicated for these moieties and index as preferred, particularly preferred and quite particularly preferred in conjunction with the description of compounds of Formula (I) according to the invention.

The compounds of Formula (I-a) are invention-related compounds and can be prepared according to Methods (a) to (d).

The halogenides, which are further necessary for carrying out Method (e) according to the invention are generally defined by Formula (VIII). In Formula (VIII), $R^{3,4}$ preferably, particularly preferably and quite particularly preferably stand for those meanings that were already indicated above for this moiety as preferred, particularly preferred and quite particularly preferred for the compounds of Formula (I-b). $X^4$ stands for chlorine, bromine or iodine.

Halogenides of Formula (VIII) are known.

Reaction Conditions

All inert organic solvents come into consideration as diluents for carrying out Methods (a), (f) and (g) according to the invention. Preferred examples are: aliphatic, alicyclic or aromatic hydrocarbons, such as e.g. petroleum ether, hexane, heptane, cyclohexane, methylcyclohexane, benzene, toluene, xylene or decalin; halogenated hydrocarbons, such as e.g. chlorobenzene, dichlorobenzene, dichloromethane, chloroform, tetrachloromethane, dichloroethane or trichloroethane; ethers, such as diethylether, diisopropylether, methyl-t-butylether, methyl-t-amylether, dioxane, tetrahydrofuran, 1,2-dimethoxyethane, 1,2-diethoxyethane or anisole; ketones, such as acetone, butanone, methyl-isobutylketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric acid triamide; mixtures of these with water or pure water.

Methods (a), (f) and (g) according to the invention are carried out in the presence of a suitable acid acceptor, if necessary. All customary inorganic or organic bases come into consideration as such. Preferred examples are: alkaline earth metallic or alkali metallic hydrides, hydroxides, amides, alcoholates, acetates, carbonates or hydrogen carbonates, such as e.g. sodium hydride, sodium amide, lithium-diisopropylamide, sodium-methylate, sodium-ethylate, potassium-tert.-butylate, sodium hydroxide, potassium hydroxide, sodium acetate, sodium carbonate, potassium carbonate, potassium hydrogen carbonate, sodium hydrogen carbonate or ammonium carbonate, as well as tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Methods (a), (f) and (g) according to the invention are carried out in the presence of a condensation agent, if necessary. All customarily applicable condensation agents come into consideration as such. Examples are: acid halide forming agents such as phosgene, phosphorous tribromide, phosphorous trichloride, phosphorous pentachloride, phosphorous oxychloride or thionyl chloride; anhydride forming agents such as chloroformic acid ethyl ester, chloroformic acid methyl ester, chloroformic acid propyl ester, chloroformic acid butyl ester or methanesulphonylchloride; carbodiimides, such as N,N'-dicyclohexylcarbodiimide (DCC) or other customary condensation agents, such as phosphorous pentoxide, polyphosphoric acid, N,N'-carbonyldiimidazole, 2-ethoxy-N-ethoxycarbonyl-1,2-dihydroquinoline (EEDQ), triphenylphosphine/tetrachlorocarbon or bromo-tripyrrolidino-phosphonium-hexafluorophosphate.

Methods (a), (f) and (g) according to the invention are carried out in the presence of a catalyst, if necessary. Examples are: 4-dimethylaminopyridine, 1-hydroxy-benzotriazole or dimethylformamide.

The reaction temperatures can be varied within a wide range when carrying out Methods (a), (f) and (g) according to the invention. In general, the work is performed at temperatures of 0° C. to 150° C., preferably at temperatures of 0° C. to 80° C.

In order to perform Method (a) according to the invention for preparing the compounds of Formula (I), generally 0.8 to 15 Mol, preferably 0.8 to 8 Mol of the aniline derivative of Formula (III) is used per Mol of the carboxylic acid derivative of Formula (II).

In order to perform Method (f) according to the invention for preparing the compounds of Formula (IV), generally 0.8 to 15 Mol, preferably 0.8 to 8 Mol of halogen anilines of Formula (IX) are used per Mol of the carboxylic acid derivative of Formula (II).

In order to perform Method (g) according to the invention for preparing the compounds of Formula (VI), generally 0.8 to 15 Mol, preferably 0.8 to 8 Mol of the aniline boronic acid derivative of Formula (X) is used per Mol of the carboxylic acid derivative of Formula (II).

All inert organic solvents come into consideration as diluents for carrying out Methods (b), (c) and (d). Preferred examples are: aliphatic, alicyclic or aromatic hydrocarbons, such as e.g. petroleum ether, hexane, heptane, cyclohexane, methylcyclohexane, benzene, toluene, xylene or decalin; ethers, such as diethyl ether, diisopropyl ether, methyl-t-butyl ether, methyl-t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric acid triamide; esters such as acetic acid methyl ester or acetic acid ethyl ester; sulphoxides, such as dimethylsulphoxide; sulphones, such as sulpholane; alcohols, such as methanol, ethanol, n- or i-propanol, n-, i-, sec- or tert-butanol, ethanediol, propane-1,2-diol, ethoxyethanol, methoxyethanol, diethyleneglycol monomethyl ether, diethylene glycol monoethyl ether, mixtures of these with water or pure water.

When performing Methods (b), (c) and (d) according to the invention, the reaction temperatures can be varied within a wide range. In general, the work is performed at temperatures of 0° C. to 180° C., preferably at temperatures of 20° C. to 150° C.

Methods (b), (c) and (d) according to the invention are carried out in the presence of a suitable acid acceptor, if necessary. All customary inorganic or organic bases come into consideration as such. Preferred examples are: alkaline earth metallic or alkali metallic hydrides, hydroxides, amides, alcoholates, acetates, fluorides, phosphates, carbonates or hydrogen carbonates, such as e.g. sodium hydride, sodium amide, lithiumdiisopropylamide, sodium-methylate, sodium-ethylate, potassium-tert.-butylate, sodium hydroxide, potassium hydroxide, sodium acetate, sodium phosphate, potassium phosphate, potassium fluoride, caesium fluoride, sodium carbonate, potassium carbonate, potassium hydrogen carbonate, sodium hydrogen carbonate or caesium carbonate, as well as tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Methods (b), (c) and (d) according to the invention are carried out in the presence of a catalyst, if necessary, such as e.g. a palladium salt or palladium complex. Preferred examples are: palladium chloride, palladium acetate, tetrakis-(triphenylphosphine)palladium, bis(triphenylphosphine)palladium dichloride or (1,1'-bis(diphenylphosphino)ferrocene palladium (II) chloride).

A palladium complex can also be created in the reaction mixture, if a palladium salt and a complex ligand, such as e.g. triethylphosphane, tri-tert-butylphosphane, tricyclohexylphosphane, 2-(dicyclohexylphosphane)-biphenyl, 2-(di-tert-butylphosphane)-biphenyl, 2-(dicyclohexylphosphane)-2'-(N,N-dimethylamino)-biphenyl, triphenylphosphane, tris-(o-tolyl)-phosphane, sodium-3-(diphenylphosphino) benzene sulphonate, tris-2-(methoxyphenyl)-phosphane, 2,2'-bis-(diphenylphosphane)-1,1'-binaphthyl, 1,4-bis-(diphenylphosphane)-butane, 1,2-bis-(diphenylphosphane)-ethane, 1,4-bis(dicyclohexylphosphane)-butane, 1,2-bis-(dicyclohexylphosphane)-ethane, 2-(dicyclohexylphosphane)-2'-(N,N-dimethylamino)-biphenyl, bis-(diphenylphosphino) ferrocene or tris-(2,4-tert-butylphenyl)-phosphite, are separately added to the reaction.

In order to perform Method (b) according to the invention for preparing the compounds of Formula (I), generally 1 to 15 Mol, preferably 2 to 8 Mol of boronic acid derivatives of Formula (V) are used per Mol of the halogen carboxamide of Formula (IV).

In order to perform Method (c) according to the invention for preparing the compounds of Formula (I), generally 0.8 to 15 Mol, preferably 0.8 to 8 Mol of phenyl derivatives of Formula (VII) are used per Mol of the boronic acid derivative of Formula (VI).

In order to perform Method (d) according to the invention for preparing the compounds of Formula (I), generally 0.8 to 15 Mol, preferably 0.8 to 8 Mol of the phenyl derivative of Formula (VII) and 0.8 to 15 Mol, preferably 0.8 to 8 Mol of 4,4,4',4',5,5,5',5'-octamethyl-2,2'-bis-1,3,2-dioxaborolane are used per Mol of the halogen carboxamide of Formula (IV).

All inert organic solvents come into consideration as diluents for performing Method (e) according to the invention. Preferred examples are: aliphatic, alicyclic or aromatic hydrocarbons, such as e.g. petroleum ether, hexane, heptane, cyclohexane, methylcyclohexane, benzene, toluene, xylene or decalin; halogenated hydrocarbons, such as e.g. chlorobenzene, dichlorobenzene, dichloromethane, chloroform, tetrachloromethane, dichloroethane or trichloroethane; ethers, such as diethyl ether, diisopropyl ether, methyl-tert-butyl ether, methyl-tert-amyl ether, dioxane, tetrahydrofuran, 1,2-dimethoxyethane, 1,2-diethoxyethane or anisole or amides, such as N,N-dimethylformamide, N,N-dimethylacetamide, N-methylformanilide, N-methylpyrrolidone or hexamethylphosphoric acid triamide.

Method (e) according to the invention is carried out in the presence of a base. All customary inorganic or organic bases come into consideration as such. Preferred examples are: alkaline earth metallic or alkali metallic hydrides, hydroxides, amides, alcoholates, acetates, carbonates or hydrogen carbonates, such as e.g. sodium hydride, sodium amide, sodium-methylate, sodium-ethylate, potassium-tert.-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or caesium carbonate, as well as tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When performing Method (e) according to the invention, the reaction temperatures can be varied within a wide range. In general, the work is performed at temperatures of 0° C. to 150° C., preferably at temperatures of 20° C. to 110° C.

In order to perform Method (e) according to the invention for preparing the compounds of Formula (I), generally 0.2 to 5 Mol, preferably 0.5 to 2 Mol of the halogenide of Formula (VIII) is used per Mol of the biphenyl thiazole carboxamide of Formula (I-a).

If nothing else is indicated, all methods according to the invention are generally performed at normal pressure. However, it is possible to perform the work at increased or decreased pressures—generally between 0.1 bar and 10 bar.

The invention-related substances exhibit a strong microbicidal effect and can be used for combating undesired microorganisms, such as fungi and bacteria, in the areas of plant protection and material protection.

Fungicides can be used in the area of plant protection for combating Plasmodiophoromycetes, Oomycetes, Chytridiomycetes, Zygomycetes, Ascomycetes, Basidiomycetes and Deuteromycetes. Bactericides can be used in the area of plant protection for combating Pseudomonadaceae, Rhizobiaceae, Enterobacteriaceae, Corynebacteriaceae and Streptomycetaceae.

The following pathogens of fungal and bacterial diseases that fall under the abovementioned genera are mentioned as examples, however they should not be considered all-inclusive:
Xanthomonas species, such as e.g. Xanthomonas campestris pv. oryzae;
Pseudomonas species, such as e.g. Pseudomonas syringae pv. lachrymans;
Erwinia species, such as e.g. Erwinia amylovora;
Pythium species, such as e.g. Pythium ultimum;
Phytophthora species, such as e.g. Phytophthora infestans;
Pseudoperonospora species, such as e.g. Pseudoperonospora humuli or Pseudoperonospora cubensis;
Plasmopara species, such as e.g. Plasmopara viticola;
Bremia species, such as e.g. Bremia lactucae;
Peronospora species, such as e.g. Peronospora pisi or P. brassicae;
Erysiphe species, such as e.g. Erysiphe graminis;
Sphaerotheca species, such as e.g. Sphaerotheca fuliginea;
Podosphaera species, such as e.g. Podosphaera leucotricha;
Venturia species, such as e.g. Venturia inaequalis;
Pyrenophora species, such as e.g. Pyrenophora teres or P. graminea
(conidial form: Drechslera, syn: Helminthosporium);
Cochliobolus species, such as e.g. Cochliobolus sativus
(conidial form: Drechslera, syn: Helminthosporium);
Uromyces species, such as e.g. Uromyces appendiculatus;
Puccinia species, such as e.g. Puccinia recondita;
Sclerotinia species, such as e.g. Sclerotinia sclerotiorum;
Tilletia species, such as e.g. Tilletia caries;
Ustilago species, such as e.g. Ustilago nuda or Ustilago avenae;
Pellicularia species, such as e.g. Pellicularia sasakii;
Pyricularia species, such as e.g. Pyricularia oryzae;
Fusarium species, such as e.g. Fusarium culmorum;
Botrytis species, such as e.g. Botrytis cinerea;
Septoria species, such as e.g. Septoria nodorum;
Leptosphaeria species, such as e.g. Leptosphaeria nodorum;
Cercospora species, such as e.g. Cercospora canescens;
Alternaria species, such as e.g. Alternaria brassicae;
Pseudocercosporella species, such as e.g. Pseudocercosporella herpotrichoides;
Rhizoctonia species, such as e.g. Rhizoctonia solani.

The invention-related substances exhibit a strong fortifying effect in plants. Therefore, they are suitable for mobilising the plants' own defenses against contamination by undesired microorganisms.

In the present context, plant-fortifying (resistance-inducing) substances are to be understood as those substances that are capable of stimulating the defense system in plants in such a way that the treated plants develop considerable resistance to these microorganisms following subsequent inoculation.

In the present context, undesired microorganisms are to be understood to be phytopathogenic fungi, bacteria, and viruses. The invention-related substances can also be used to protect plants against contamination by the named pathogens for a certain time period following treatment. The time period, for which this protection is provided, generally ranges from 1 to 10 days, preferably 1 to 7 days following treatment of the plants with the active compounds.

The good plant tolerance of the active compounds according to the invention at the concentrations required for controlling plant diseases allows treatment of above-ground parts of plants, of propagation stock and seeds, and of the soil.

The active compounds according to the invention can be employed particularly successfully for controlling cereal diseases, such as, for example, against Puccinia species, diseases in viticulture and fruit and vegetable production such as, for example, against *Botrytis, Venturia* or *Alternaria* species.

The active compounds according to the invention are also suitable for increasing the harvest yield. Moreover, they exhibit low toxicity and are well tolerated by plants.

The active compounds according to the invention can also be used in certain concentrations and at certain application rates as herbicides, for influencing plant growth rates, and for combating animal pests, if applicable. They can also be used as intermediate products and preliminary products for the synthesis of additional active compounds, if applicable.

All plants and plant parts can be treated with the substances according to the invention. Plants in this context are taken to mean all plants and plant populations, such as desired and undesired wild plants or crop plants (including naturally occurring crop plants). Crop plants can be plants which can be obtained by conventional breeding and optimisation methods, or by biotechnological and genetic engineering methods, or by combinations of these methods, including the transgenic plants and including the plant varieties which are capable, or incapable, of being protected by Plant Breeders' Rights. Plant parts are to be taken to mean all above-ground and below-ground parts and organs of the plants, such as the shoot, leaf, flower and root; examples mentioned being leaves, needles, stalks, stems, flowers, fruit bodies, fruits and seeds, and also roots, tubers and rhizomes. The plant parts also include harvested material and vegetative and generative propagation material, for example cuttings, tubers, rhizomes, offshoots and seeds.

The invention-related treatment of the plants and plant parts with the active compounds occurs directly or by affecting the environment, habitat or storage area according to customary treatment methods, e.g. by dipping, spraying, vaporising, atomising, scattering, brushing on, and in the case of propagation material, particularly in the case of seeds, by further encasing it with one or more layers.

In the area of material protection, the compounds according to the invention can be employed for protecting industrial materials against infection with, and destruction by, undesirable microorganisms.

Industrial materials in the present context are understood to mean non-living materials, which have been prepared for use in industry. For example, industrial materials which are intended to be protected by active compounds according to the invention from microbial change or destruction can be glues, pastes, paper and cardboard, textiles, leather, wood, paints and synthetic articles, cooling lubricants and other materials which can be infected with, or destroyed by, microorganisms. Parts of production plants, for example cooling-water circuits, which may be impaired by the multiplication of microorganisms may also be mentioned within the scope of the materials to be protected. Industrial materials, which may be mentioned within the scope of the present invention, are preferably glues, pastes, paper and cardboard, leather, wood, paints, cooling lubricants and heat-transfer liquids, particularly preferably wood.

The following are mentioned as examples of microorganisms that can cause a decomposition or change in industrial materials: bacteria, fungi, yeasts, algae and slime organisms. The active compounds according to the invention preferably have an effect on fungi, particularly moulds, wood-discolouring and wood-destroying fungi (Basidiomycetes) as well as on slime organisms and algae.

Microorganisms of the following genera may be mentioned by way of example:
*Alternaria*, such as *Alternaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*,
*Staphylococcus*, such as *Staphylococcus aureus*.

Depending on their respective physical and/or chemical characteristics, the active compounds can be converted into the customary formulations, such as solutions, emulsions, suspensions, powders, foams, pastes, granules, aerosols, fine encapsulations in polymer substances and in coatings for seeds, as well as ULV cold and warm fog formulations.

These formulations are produced in a known manner, e.g. by mixing the active compounds with extenders, or liquid solvents, liquefied gases under pressure and/or solid carrier substances, while using surface active agents if applicable, or emulsifiers and/or dispersants and/or foam-producing agents. If water is used as an extender, organic solvents can also be used as auxiliary solvents, for example. The following fundamentally come into consideration as liquid solvents: aromates, such as xylene, toluene or alkylnaphthalines, chlorated aromates or chlorated aliphatic hydrocarbons, such as chlorobenzenes, chloroethylenes or methylenechloride, aliphatic hydrocarbons, such as cyclohexane or paraffins, e.g. petroleum fractions, alcohols, such as butanol or glycol as well as their ethers and esters, ketones, such as acetone, methylethylketone, methylisobutylketone or cyclohexanone, strongly polar solvents, such as dimethylformamide and dimethylsulphoxide, as well as water. With liquefied gaseous extenders or carrier substances, those liquids are meant, which are gaseous at normal temperatures and normal pressure, e.g. aerosol propellants, such as halogen hydrocarbons as well as butane, propane, nitrogen and carbon dioxide. Suitable solid carriers are: for example, ground natural minerals such as kaolins, clays, talc, chalk, quartz, attapulgite, montmorillonite or diatomaceous earth, and ground synthetic minerals such as highly dispersed silicic acid, aluminium oxide and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam-producing agents are: for example, non-ionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example, lignin sulphite waste liquors and methylcellulose.

Adhesives such as carboxymethylcellulose, and natural and synthetic polymers in the form of powders, granules or latex, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention, as such or in their formulations, can also be used in a mixture with known fungicides, bactericides, acaricides, nematicides or insecticides, for example to widen the spectrum of action or to prevent the development of resistance. In many cases, synergistic effects are obtained, that is the activity of the mixture is greater than the activity of the individual components.

Examples of suitable components in mixtures are the following

Fungicides:

2-phenylphenol; 8-hydroxyquinoline sulphate; acibenzolar-S-methyl; aldimorph; amidoflumet; ampropylfos; ampropylfos-potassium; andoprim; anilazin; azaconazole; azoxystrobin; benalaxyl; benalaxyl-M; benodanil; benomyl; benthiavalicarb-isopropyl; benzamacril; benzamacril-isobutyl; bilanafos; binapacryl; biphenyl; bitertanol; blasticidin-S; boscalid; bromuconazole; bupirimate; buthiobate; butylamine; calcium polysulphide; capsimycin; captafol; captan; carbendazim; carboxin; carpropamid; carvone; quinomethionate; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadon; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulphamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulphocarb; methfuroxam; metiram; metominostrobin; metsulphovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazol; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrine; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)—N-[2-[4-[[3-(4-chlorophenyl)-2-propynyl]oxy]-3-methoxyphenyl]ethyl]-3-methyl-2-[(methylsulphonyl)amino]-butanamide; 1-(1-naphthalinyl)-1H-pyrrol-2,5-dione; 2,3,5,6-tetrachloro-4-(methylsulphonyl)-pyridine; 2-amino-4-methyl-N-phenyl-5-thiazolecarboxamide; 2-chloro-N-(2,3-dihydro-1,1,3-trimethyl-1H-indene-4-yl)-3-pyridinecarboxamide; 3,4,5-trichloro-2,6-pyridinedicarbonitrile; actinovate; cis-1-(4-chlorophenyl)-2-(1H-1,2,4-triazole-1-yl)-cycloheptanol; methyl 1-(2,3-dihydro-2,2-dimethyl-1H-indene-1-yl)-1H-imidazole-5-carboxylate; monopotassiumcarbonate; N-(6-methoxy-3-pyridinyl)-cyclopropanecarboxamide; N-butyl-8-(1,1-dimethylethyl)-1-oxaspiro[4.5]decane-3-amine; sodiumtetracarbonate;

as well as copper salts and preparation, such as Bordeaux mixture; copper hydroxide; copper naphthenate; copper oxychloride; copper sulphate; cufraneb; cuprous oxide; mancopper; oxine-copper.

Bactericides:

Bronopol, dichlorophen, nitrapyrin, nickel-dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:

1. Acetylcholine Esterase (AChE) Inhibitors 1.1 Carbamates (e.g. alanycarb, aldicarb, aldoxycarb, allyxycarb, aminocarb, azamethiphos, bendiocarb, benfuracarb, bufencarb, butacarb, butocarboxim, butoxycarboxim, carbaryl, carbofuran, carbosulphan, chloethocarb, coumaphos, cyanofenphos, cyanophos, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, triazamate, trimethacarb, XMC, xylylcarb)

1.2 Organophosphates (e.g. acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-5-methyl, demeton-5-methylsulphon, dialifos, diazinon, dichlofenthion, dichlorvos/DDVP, dicrotophos, dimethoate, dimethylvinphos, dioxabenzofos, disulphoton, EPN, ethion, ethoprophos, etrimfos, famphur, fenamiphos, fenitrothion, fensulphothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion)

2. Sodium Channel Modulators/Voltage-Dependent Sodium Channel Blockers 2.1 Pyrethroids (e.g. acrinathrin, allethrin (d-cis-trans, d-trans), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralomethrin, transfluthrin, ZXI 8901, pyrethrins (pyrethrum))
    2.2 Oxadiazines (e.g. indoxacarb)
3. Acetylcholine Receptor Agonists/Acetylcholine Receptor Antagonists
    3.1 Chloronicotinyls/neonicotinoids (e.g. acetamiprid, clothianidin, dinotefuran, imidacloprid, nitenpyram, nithiazine, thiacloprid, thiamethoxam)
    3.2 Nicotine, bensultap, cartap
4. Acetylcholine Receptor Modulators
    4.1 Spinosyns (e.g. spinosad)
5. GABA-Gated Chloride Channel Antagonists
    5.1 Cyclodiene organochlorines (e.g. camphechlor, chlordane, endosulphan, gamma-HCH, HCH, heptachlor, lindane, methoxychlor
    5.2 Fiproles (e.g. acetoprole, ethiprole, fipronil, vaniliprole)
6 Chloride Channel Activators
    6.1 Mectins (e.g. abamectin, avermectin, emamectin, emamectin-benzoate, ivermectin, milbemectin, milbemycin)
7. Juvenile Hormone Mimics
(e.g. diofenolan, epofenonane, fenoxycarb, hydroprene, kinoprene, methoprene, pyriproxifen, triprene)
8. Ecdysone Agonists/Disruptors
    8.1 Diacylhydrazines (e.g. chromafenozide, halofenozide, methoxyfenozide, tebufenozide)
9. Chitin Biosynthesis Inhibitors
    9.1 Benzoyl urea compounds (e.g. bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron)
    9.2 Buprofezin
    9.3 Cyromazine
10. Oxidative Phosphorylation Inhibitors, ATP-Disruptors
    10.1 Diafenthiuron
    10.2 Organotines (e.g. azocyclotin, cyhexatin, fenbutatinoxide)
11. Oxidative Phosphorylation Decouplers Through Interruption of the H-Proton Gradient
    11.1 Pyrroles (e.g. chlorfenapyr)
    11.2 Dinitrophenols (e.g. binapacyrl, dinobuton, dinocap, DNOC)
12. Site I Electron Transport Inhibitors
    12.1 METI's (e.g. fenazaquin, fenpyroximate, pyrimidifen, pyridaben, tebufenpyrad, tolfenpyrad)
    12.2 Hydramethylnone
    12.3 Dicofol
13. Site II Electron Transport Inhibitors
    13.1 Rotenone
14. Site III Electron Transport Inhibitors
    14.1 Acequinocyl, Fluacrypyrim
15. Microbial Disruptors of the Insect Midgut Membrane
    *Bacillus thuringiensis* strains
16 Lipid Synthesis Inhibitors
    16.1 Tetronic acids (e.g. spirodiclofen, spiromesifen)
    16.2 Tetramic acids [e.g. 3-(2,5-dimethylphenyl)-8-methoxy-2-oxo-1-azaspiro[4.5]dec-3-ene-4-yl ethyl carbonate (alias: carbonic acid, 3-(2,5-dimethylphenyl)-8-methoxy-2-oxo-1-azaspiro[4.5]dec-3-ene-4-yl ethyl ester, CAS-Reg.-No.: 382608-10-8) and carbonic acid, cis-3-(2,5-dimethylphenyl)-8-methoxy-2-oxo-1-azaspiro[4.5]dec-3-ene-4-yl ethyl ester (CAS-Reg.-No.: 203313-25-1)]
17. Carboxamides
(e.g. flonicamide)
18. Octopaminergic Agonists
(e.g. amitraz)
19. Magnesium-Stimulated ATPase Inhibitors
(e.g. propargite)
20. Phthalamides
(e.g. $N^2$-[1,1-dimethyl-2-(methylsulphonyl)ethyl]-3-iodo-$N^1$-[2-methyl-4-[1,2,2,2-tetrafluoro-1-(trifluoromethyl)ethyl]phenyl]-1,2-benzenedicarboxamide (CAS-Reg.-No.: 272451-65-7), flubendiamide)
21. Nereistoxin Analogues
(e.g. thiocyclam hydrogen oxalate, thiosultap-sodium)
22. Biologics, Hormones or Pheromones
(e.g. azadirachtin, *Bacillus* spec., *Beauveria* spec., codlemone, *Metarrhizium* spec., *Paecilomyces* spec., thuringiensin, *Verticillium* spec.)
23. Active Compounds with Unknown or Non-Specific Mode of Action
    23.1 Fumigants (e.g. aluminium phosphide, methyl bromide, sulphuryl fluoride)
    23.2 Selective feeding blockers (e.g. cryolite, flonicamide, pymetrozine)
    23.3 Mite growth inhibitors (e.g. clofentezine, etoxazole, hexythiazox)
    23.4 Amidoflumet, benclothiaz, benzoximate, bifenazate, bromopropylate, buprofezin, quinomethionate, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulphluramide, tetradifon, tetrasul, triarathene, verbutin, as well as the compound 3-methyl-phenyl-propylcarbamate (tsumacide Z), the compound 3-(5-chloro-3-pyridinyl)-8-(2,2,2-trifluoroethyl)-8-azabicyclo[3.2.1]octane-3-carbonitrile (CAS-Reg.-Nr. 185982-80-3) and the corresponding 3-endo-isomers (CAS-Reg.-Nr. 185984-60-5) (see WO 96/37494, WO 98/25923), as well as preparations, which contain insecticidal plant extracts, nematodes, fungi or viruses.

A mixture with other known active compounds such as herbicides, or with fertilisers and growth regulators, safeners or semiochemicals is also possible.

In addition, the compounds of Formula (I) according to the invention also have very good antimycotic activity. They have a very broad antimycotic activity spectrum in particular against dermatophytes and yeasts, moulds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*. The list of these fungi by no means limits the mycotic spectrum covered, but is only for illustration.

The active compounds can be used as such, in the form of their formulations or the usage forms prepared from them, such as ready-to-use solutions, suspensions, soluble powders, pastes, soluble powders, dusts and granules. Application is carried out in a customary manner, for example by watering, spraying, atomising, scattering, dusting, foaming, spreading, etc. It is furthermore possible to apply the active compounds by the ultra-low-volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1,000 g/ha. For seed dressing, the active compound application rates are generally between 0.001 and 50 g per kilogram of seed, preferably between 0.01 and 10 g per kilogram of seed. For treatment of the soil, the active compound application rates are generally between 0.1 and 10,000 g/ha, preferably between 1 and 5,000 g/ha.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars, which are in each case commercially available or in use, are treated according to the invention. Plant cultivars are understood to mean plants with novel characteristics ("traits"), which are grown by conventional cultivation, by mutagenesis or by recombinant DNA techniques. These may be pure species, cultivars, biotypes or genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible, which exceed the effects that were actually expected.

The transgenic plants or plant cultivars (i.e. those obtained by genetic engineering), which are preferably to be treated according to the invention include all plants which, in the genetic modification, received genetic material, which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, Soya beans, potatoes, cotton, tobacco, oilseed rape and also fruit plants (with the fruits apples, pears, citrus fruits and grapes), and particular emphasis is given to maize, Soya beans, potatoes, cotton, tobacco and oilseed rape. Traits that are emphasized are in particular increased defense of the plants against insects, arachnids, nematodes and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinafter referred to as "Bt plants"). Traits, which are also particularly emphasised, are the increased resistance of plants to fungi, bacteria and viruses by systemic acquired resistance (SAR), systemin, phytoalexins, elicitors and resistance genes and the correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes, which impart the desired traits in question, can also be present in combination with one another in the transgenic plants. Examples of "Bt plants" which may be mentioned are maize varieties, cotton varieties, Soya bean varieties and potato varieties which are sold under the trade names YIELD GARD® (for example maize, cotton, Soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and Soya bean varieties which are sold under the trade names Roundup Ready® (tolerance to glyphosate, for example maize, cotton, Soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance), which may be mentioned, include the varieties sold under the name Clearfield® (for example maize). Of course, these statements also apply to plant cultivars having these genetic traits or genetic traits still to be developed, which will be developed and/or marketed in the future.

The plants listed can be treated according to the invention in a particularly advantageous manner with the compounds of Formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The preparation and the use of the active compounds according to the invention are illustrated by the following examples.

PREPARATION EXAMPLES

Example 1

Compound 2.18

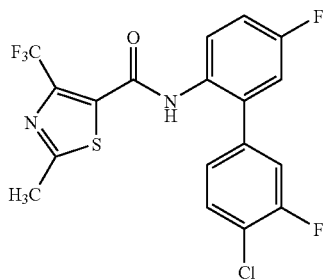

0.10 ml (1.1 mmol) oxalylchloride and 0.1 ml dimethylformamide are added to a solution consisting of 211.2 mg (1.0 mmol) 2-methyl-4-trifluoromethyl-thiazole-5-carboxylic acid in 9 ml dichloromethane. After stirring for 2 hours at room temperature, this solution is added to a solution consisting of 240.0 mg (1.0 mmol) 4'-chloro-5,3'-difluoro-biphenyl-2-yl-amine and 0.18 ml (1.3 mmol) triethylamine in 9 ml dichloromethane. The reaction mixture is stirred for 16 hours at room temperature and subsequently mixed with 7 ml 2 N hydrochloric acid. The organic phase is dried over magnesium sulphate and concentrated in vacuum.

The reaction yields 316.5 mg (73% of the theoretical yield) of N-(4'-chloro-3',5-difluorobiphenyl-2-yl)-2-methyl-4-(trifluoromethyl)-1,3-thiazole-5-carboxamide [log P (pH 2.3)= 3.67].

Preparation of Initial Substances of Formula (III)

Example (III-1)

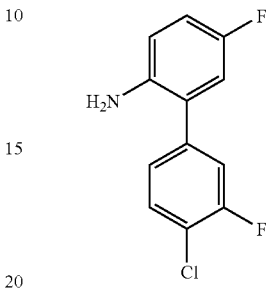

30.0 g (0.172 mol) 4-chloro-3-fluoro-phenylboronic acid and 29.7 g (0.156 mol) 2-bromo-4-fluoroaniline, in an oxygen-free atmosphere, are suspended in a mixture of 170 ml toluene, 17 ml ethanol and 160 ml of saturated sodium carbonate solution in an argon atmosphere. 3.6 g tetrakis(triphenylphosphine) palladium (0) is added to the reaction mixture, and it is stirred for 12 hours at 80° C. The organic phase is separated and the aqueous phase is extracted with acetic acid ethyl ester. The combined organic phases are concentrated, and the residue is chromatographed with cyclohexane/acetic acid ethyl ester (3:1) on silica gel.

The reaction yields 26.1 g (69.7% of the theoretical yield) of 4'-chloro-3',5-difluorobiphenyl-2-amine [log P (pH 2.3)= 3.18].

Analogously to the above example and in accordance with the general preparation procedures, the compounds listed in Table 2 below can be obtained.

TABLE 2

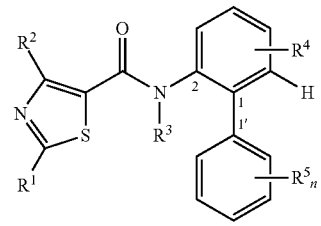

(I)

| No. | $R^1$ | $R^2$ | $R^3$ | $R^4$ | $R^5$ | Log P/Fp. (° C.) |
|---|---|---|---|---|---|---|
| 2.01 | $CH_3$ | $CF_3$ | H | 4-Cl | 3'-CH=CH—CH=CH-4' | 4.60 |
| 2.02 | $CH_3$ | $CF_3$ | H | 4-Cl | 3',4'-$Cl_2$ | 4.60 |
| 2.03 | $CH_3$ | $CF_3$ | H | 4-Cl | 3',4'-$F_2$ | 4.00 |
| 2.04 | $CH_3$ | $CF_3$ | H | 4-Cl | 3',5'-$(CH_3)_2$ | 4.80 |
| 2.05 | $CH_3$ | $CF_3$ | H | 5-$OCH_3$ | 3',4'-$Cl_2$ | 3.70 |
| 2.06 | $CH_3$ | $CF_3$ | H | 5-$OCH_3$ | 3',4'-$F_2$ | 3.60 |
| 2.07 | $CH_3$ | $CF_3$ | H | 5-$OCH_3$ | 2',4'-$F_2$ | 3.50 |
| 2.08 | $CH_3$ | $CF_3$ | H | 5-$OCH_3$ | 2',5'-$Cl_2$ | 4.20 |
| 2.09 | $CH_3$ | $CF_3$ | H | 5-$OCH_3$ | 3',5'-$(CF_3)_2$ | 3.70 |
| 2.10 | $CH_3$ | $CF_3$ | H | 5-$OCH_3$ | 3',5'-$Cl_2$ | 3.20 |
| 2.11 | $CH_3$ | $CF_3$ | H | 5-F | 3',4'-$Cl_2$ | 3.93 |
| 2.12 | $CH_3$ | $CHF_2$ | H | 5-F | 3',4'-$Cl_2$ | 3.63 |
| 2.13 | $CH_3$ | $CHF_2$ | H | 3-F | 3',4'-$Cl_2$ | 3.43 |
| 2.14 | $CH_3$ | $CF_3$ | H | 3-F | 3',4'-$Cl_2$ | 3.68 |
| 2.15 | $CH_3$ | $CF_3$ | H | 3-F | 3'-F, 4'-Cl | 3.39 |
| 2.16 | $CH_3$ | $CHF_2$ | H | 3-F | 3'-F, 4'-Cl | 3.16 |
| 2.17 | $CH_3$ | $CHF_2$ | H | 5-F | 3'-F, 4'-Cl | 3.36 |
| 2.18 | $CH_3$ | $CF_3$ | H | 5-F | 3'-F, 4'-Cl | 3.67 |

TABLE 2-continued (I)

Structure: thiazole with R¹ at 2-position, R² at 4-position, 5-carboxamide N(R³) connected to biphenyl with R⁴ and H on first ring (position 2 attached to N, position 1 attached to 1'), and R⁵ₙ on second ring.

| No. | R¹ | R² | R³ | R⁴ | R⁵ | Log P/Fp. (° C.) |
|---|---|---|---|---|---|---|
| 2.19 | $CH_3$ | $CHF_2$ | H | 5-F | 2'-F, 3'-Cl | 3.24 |
| 2.20 | $CH_3$ | $CF_3$ | H | 5-F | 3'-$CH_3$, 4'-Cl | 3.99 |
| 2.21 | $CH_3$ | $CHF_2$ | H | 5-F | 3'-$CH_3$, 4'-Cl | 3.68 |
| 2.22 | $N(CH_3)_2$ | $CF_3$ | H | 4-Cl | 2',4'-$Cl_2$ | 5.04 |
|  |  |  |  |  |  | 132-134° C. |
| 2.23 | $N(CH_3)_2$ | $CF_3$ | H | 5-F | 3'-$CH_3$, 4'-Cl | 4.42 |
| 2.24 | $N(CH_3)_2$ | $CF_3$ | H | 5-F | 3',4'-$Cl_2$ | 4.32 |
| 2.25 | $CH_3$ | $CHF_2$ | H | 5-F | 3'-F, 4'-$CH_3$ | 3.37 |
| 2.26 | $CH_3$ | $CF_3$ | H | 5-F | 3'-F, 4'-$CH_3$ | 3.70 |
| 2.27 | $CH_3$ | $CF_3$ | H | 5-F | 3'-Cl, 4'-$CH_3$ | 2.27 |
| 2.28 | $CH_3$ | $CHF_2$ | H | 5-F | 3'-Cl, 4'-$CH_3$ | 2.28 |

The determination of the Log P values occurred according to EEC Directive 79/831, Annex V.A8 using HPLC (High Performance Liquid Chromatography) on a reversed-phase column (C 18). Temperature: 43° C.

Eluents for determination in the acidic range (pH 2.3): 0.1% aqueous phosphoric acid, acetonitrile; linear gradient of 10% acetonitrile to 90% acetonitrile.

Calibration took place using unbranched alkane-2-ones (with 3 to 16 carbon atoms) with known Log P values (the Log P values were determined on the basis of the retention times by way of linear interpolation between two consecutive alkanones).

The λ max values were calculated on the basis of 200 nm to 400 nm UV spectra in the maxima of the chromatographic signals.

EXAMPLES OF USE

Example A

*Podosphaera* Test (Apple)/Protective

| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

In order to test the protective activity, young plants are sprayed with the active compound preparation at the stated application rate. After the spray coating dries, the plants are inoculated with an aqueous spore suspension of *Podosphaera leucotricha*. The plants are then placed in the greenhouse at approx. 23° C. and at a relative humidity of approx. 70%.

The results are evaluated 10 days after the inoculation. An efficacy of 0% corresponds to that of the control, while an efficacy of 100% means that no infestation is observed.

TABLE A

Podosphaera Test (Apple)/Protective

| Active Compound According to the Invention | Application Rate of Active Compound in g/ha | Efficacy in % |
|---|---|---|
| (2.12) structure | 100 | 100 |
| (2.13) structure | 100 | 100 |

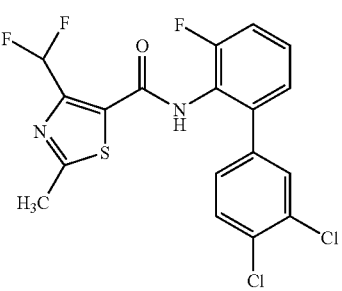

TABLE A-continued

Podosphaera Test (Apple)/Protective

| Active Compound According to the Invention | Application Rate of Active Compound in g/ha | Efficacy in % |
|---|---|---|
| (2.11) | 100 | 100 |
| (2.14) | 100 | 100 |
| (2.16) | 100 | 100 |
| (2.18) | 100 | 100 |
| (2.20) | 100 | 100 |
| (2.21) | 100 | 100 |
| (2.19) | 100 | 94 |

Example B

Venturia Test (Apple)/Protective

| | |
|---|---|
| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

In order to test the protective activity, young plants are sprayed with the active compound preparation at the stated application rate. After the spray coating dries, the plants are inoculated with an aqueous conidial suspension of the apple scab fungus *Venturia inaequalis* and then remain in an incubation cabinet for 1 day at approx. 20° C. and 100% relative humidity.

The plants are then placed in the greenhouse at approx. 21° C. and at a relative humidity of approx. 90%.

The results are evaluated 10 days after the inoculation. An efficacy of 0% corresponds to that of the control, while an efficacy of 100% means that no infestation is observed.

TABLE B

| Venturia Test (Apple)/Protective | | |
|---|---|---|
| Active Compound According to the Invention | Application Rate of Actve Compound in g/ha | Efficacy in % |
| 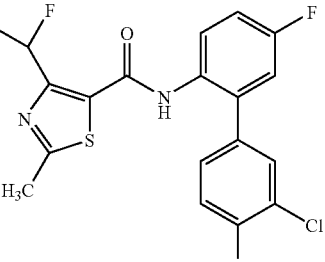 (2.12) | 100 | 100 |
| 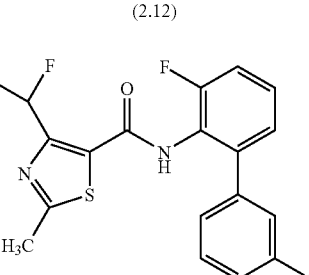 (2.13) | 100 | 100 |
| 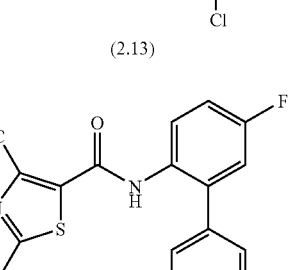 (2.11) | 100 | 100 |
| 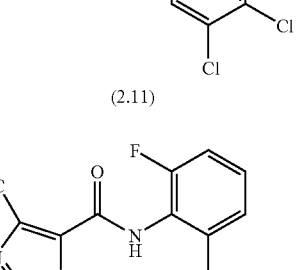 (2.14) | 100 | 100 |

TABLE B-continued

| Venturia Test (Apple)/Protective | | |
|---|---|---|
| Active Compound According to the Invention | Application Rate of Actve Compound in g/ha | Efficacy in % |
| 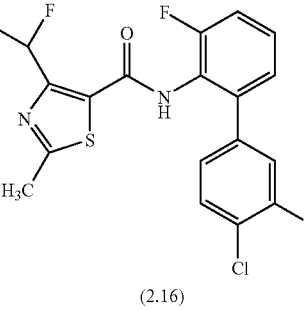 (2.16) | 100 | 100 |
| 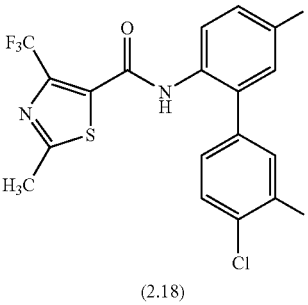 (2.18) | 100 | 100 |
| 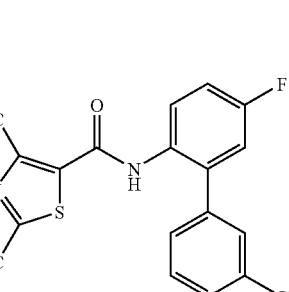 (2.20) | 100 | 100 |
| 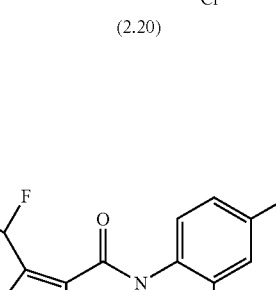 (2.21) | 100 | 100 |

TABLE B-continued

Venturia Test (Apple)/Protective

| Active Compound According to the Invention | Application Rate of Actve Compound in g/ha | Efficacy in % |
|---|---|---|
| (2.19) | 100 | 98 |

Example C

Botrytis Test (Bean)/Protective

| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

In order to test the protective activity, young plants are sprayed with the active compound preparation at the stated application rate. After the spray coating dries, 2 small pieces of agar that are infested with *Botrytis cinerea* are placed on each leaf. The inoculated plants are placed in a darkened chamber at 20° C. and 100% relative humidity.

The size of the infestation blotches on the leaves is evaluated 2 days after the inoculation. An efficacy of 0% corresponds to that of the control, while an efficacy of 100% means that no infestation is observed.

TABLE C

Botrytis Test (Bean)/Protective

| Active Compound According to the Invention | Application Rate of Active Compound in g/ha | Efficacy in % |
|---|---|---|
| (2.12) | 500 | 100 |
| (2.13) | 500 | 100 |
| (2.11) | 500 | 99 |
| (2.14) | 500 | 98 |
| (2.16) | 500 | 100 |

TABLE C-continued

Botrytis Test (Bean)/Protective

| Active Compound According to the Invention | Application Rate of Active Compound in g/ha | Efficacy in % |
|---|---|---|
| (2.18) | 500 | 100 |
| (2.20) | 500 | 100 |
| (2.21) | 500 | 100 |
| (2.19) | 500 | 98 |

Example D

Pyrenophora teres Test (Barley)/Protective

| Solvent: | 50 parts by weight of N,N-dimethylacetamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

In order to test the protective activity, young plants are sprayed with the active compound preparation at the stated application rate. After the spray coating dries, the plants are sprayed with a conidial suspension of *Pyrenophora teres*. The plants remain in an incubation cabinet for 48 hours at 20° C. and 100% relative humidity.

The plants are then placed in a greenhouse at a temperature of approx. 20° C. and a relative humidity of 80%.

The results are evaluated 7 days after the inoculation. An efficacy of 0% corresponds to that of the control, while an efficacy of 100% means that no infestation is observed.

TABLE D

Pyrenophora teres Test (Barley)/Protective

| Active Compound According to the Invention | Application Rate of Active Compound in g/ha | Efficacy in % |
|---|---|---|
| (2.12) | 500 | 100 |
| (2.16) | 500 | 100 |

TABLE D-continued

Pyrenophora teres Test (Barley)/Protective

| Active Compound According to the Invention | Application Rate of Active Compound in g/ha | Efficacy in % |
|---|---|---|
| 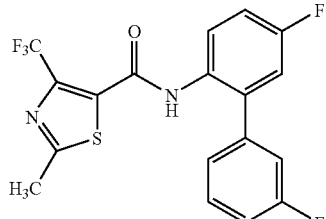 (2.18) | 500 | 100 |
| 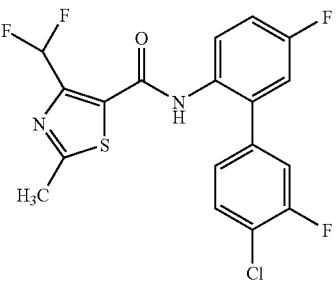 (2.17) | 500 | 100 |
| 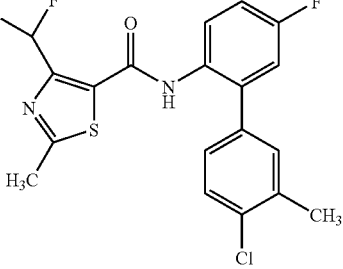 (2.21) | 500 | 100 |
| 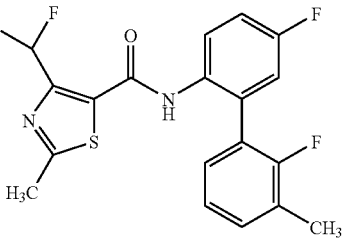 (2.19) | 500 | 100 |

Example E

Alternaria Test (Tomato)/Protective

| Solvent: | 49 parts by weight of N,N-dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

In order to test the protective activity, young tomato plants are sprayed with the active compound preparation at the stated application rate. One day after treatment, the plants are inoculated with a spore suspension of *Alternaria solani* and then remain for 24 hours at 100% relative humidity and 20° C. The plants are then placed into in environment of 96% relative humidity at a temperature of 20° C.

The results are evaluated 7 days after the inoculation. An efficacy of 0% corresponds to that of the control, while an efficacy of 100% means that no infestation is observed.

TABLE E

Alternaria Test (Tomato)/Protective

| Active Compound According to the Invention | Application Rate of Active Compound in g/ha | Efficacy in % |
|---|---|---|
| 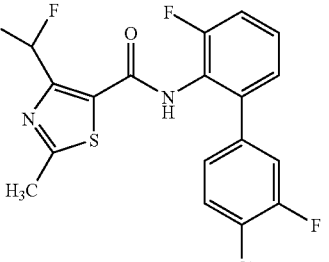 (2.16) | 750 | 100 |
| 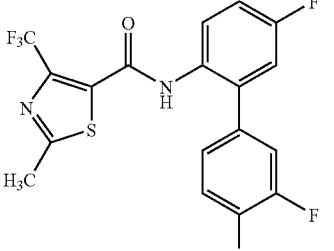 (2.18) | 750 | 100 |

TABLE E-continued

Alternaria Test (Tomato)/Protective

| Active Compound According to the Invention | Application Rate of Active Compound in g/ha | Efficacy in % |
|---|---|---|
| 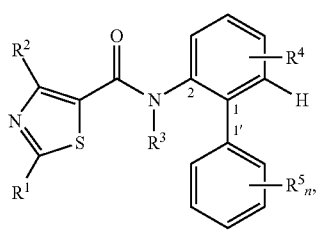 (2.17) | 750 | 98 |

The invention claimed is:

1. A compound of Formula (I)

(I)

where
- $R^1$ is hydrogen, halogen, amino, $C_1$-$C_4$-alkylamino, di-($C_1$-$C_4$-alkyl)amino, cyano, $C_1$-$C_4$-alkyl or $C_1$-$C_4$-halogenalkyl having 1 to 5 halogen atoms,
- $R^2$ is halogen, $C_1$-$C_4$-alkyl or $C_1$-$C_4$-halogenalkyl having 1 to 5 halogen atoms,
- $R^3$ is hydrogen, $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, or $C_3$-$C_8$-cycloalkyl; $C_1$-$C_6$-halogenalkyl, $C_1$-$C_4$-halogenalkylthio, $C_1$-$C_4$-halogenalkylsulphinyl, $C_1$-$C_4$-halogenalkylsulphonyl, halogen-$C_1$-$C_4$-alkoxy-$C_1$-$C_4$-alkyl, or $C_3$-$C_8$-halogencycloalkyl, each of which having 1 to 9 halogen atoms selected from the group consisting of fluorine, chlorine and bromine; formyl, formyl-$C_1$-$C_3$-alkyl, ($C_1$-$C_3$-alkyl)carbonyl-$C_1$-$C_3$-alkyl, or ($C_1$-$C_3$-alkoxy)carbonyl-$C_1$-$C_3$-alkyl; halogen-($C_1$-$C_3$-alkyl)carbonyl-$C_1$-$C_3$-alkyl, or halogen-($C_1$-$C_3$-alkoxy)carbonyl-$C_1$-$C_3$-alkyl each of which having 1 to 13 halogen atoms selected from the group consisting of fluorine, chlorine and bromine; ($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, or ($C_3$-$C_8$-cycloalkyl)carbonyl; ($C_1$-$C_6$-halogenalkyl)carbonyl, ($C_1$-$C_6$-halogenalkoxy)carbonyl, (halogen-$C_1$-$C_4$-alkoxy-$C_1$-$C_4$-alkyl)carbonyl, or ($C_3$-$C_8$-halogencycloalkyl)carbonyl, each of which having 1 to 9 halogen atoms selected from the group consisting of fluorine, chlorine and bromine; or —C(=O)C(=O)$R^6$, —CONR$^7$R$^8$ or —CH$_2$NR$^9$R$^{10}$,
- $R^4$ is halogen, $C_1$-$C_4$-alkyl, $C_1$-$C_4$-alkoxy, $C_1$-$C_4$-alkylthio or $C_1$-$C_4$-halogenalkyl having 1 to 9 halogen atoms selected from the group consisting of fluorine, chlorine and bromine,
- $R^5$ is halogen, cyano, nitro, amino, hydroxy, formyl, carboxy, carbamoyl, thiocarbamoyl, $C_1$-$C_8$-alkyl, $C_2$-$C_6$-alkenyl, $C_1$-$C_8$-alkoxy, $C_2$-$C_6$-alkenyloxy, $C_1$-$C_8$-alkylthio, $C_1$-$C_8$-alkylsulphinyl, $C_1$-$C_8$-alkylsulphonyl, $C_1$-$C_8$-hydroxyalkyl, $C_1$-$C_8$-oxoalkyl, $C_1$-$C_8$-alkoxyalkyl, $C_1$-$C_8$-alkylthioalkyl, $C_1$-$C_8$-dialkoxyalkyl, $C_1$-$C_6$-alkylamino, di($C_1$-$C_6$-alkyl)amino, ($C_1$-$C_6$-alkyl)carbonyl, ($C_1$-$C_6$-alkyl)carbonyloxy, ($C_1$-$C_6$-alkoxy)carbonyl, ($C_1$-$C_6$-alkyl)aminocarbonyl, di($C_1$-$C_6$-alkyl)aminocarbonyl, ($C_1$-$C_6$-alkyl)carbonylamino, ($C_1$-$C_6$-alkyl)carbonyl($C_1$-$C_6$-alkyl)amino, ($C_2$-$C_6$-alkenyl)carbonyl, ($C_2$-$C_6$-alkinyl)carbonyl, $C_3$-$C_6$-cycloalkyl, or $C_3$-$C_6$-cycloalkyloxy; or $C_1$-$C_6$-halogenalkyl, $C_1$-$C_6$-halogenalkoxy, $C_1$-$C_6$-halogenalkylthio, $C_1$-$C_6$-halogenalkylsulphinyl or $C_1$-$C_6$-halogenalkylsulphonyl, each of which having 1 to 13 halogen atoms, or $C_2$-$C_6$-halogenalkenyl or $C_2$-$C_6$-halogenalkenyloxy, each of which having 1 to 11 halogen atoms, which can be the same or different, or
- $R^5$ is $C_2$-$C_5$-alkenylene optionally substituted once or twice by halogen, $C_1$-$C_4$-alkyl or $C_1$-$C_4$-halogenalkyl having 1 to 5 halogen atoms, when two $R^5$ moieties are in the ortho position to each other,
- n is 2, 3, 4 or 5, wherein the $R^5$ moieties can be the same or different,
- $R^6$ is hydrogen, $C_1$-$C_8$-alkyl, $C_1$-$C_8$-alkoxy, $C_1$-$C_4$-alkoxy-$C_1$-$C_4$-alkyl, or $C_3$-$C_8$-cycloalkyl; or $C_1$-$C_6$-halogenalkyl, $C_1$-$C_6$-halogenalkoxy, halogen-$C_1$-$C_4$-alkoxy-$C_1$-$C_4$-alkyl, or $C_3$-$C_8$-halogencycloalkyl, each of which having 1 to 9 halogen atoms selected from the group consisting of fluorine, chlorine and bromine,
- $R^7$ and $R^8$, independently of one another, each are hydrogen, $C_1$-$C_8$-alkyl, $C_1$-$C_4$-alkoxy-$C_1$-$C_4$-alkyl, or $C_3$-$C_8$-cycloalkyl; or $C_1$-$C_8$-halogenalkyl, halogen-$C_1$-$C_4$-alkoxy-$C_1$-$C_4$-alkyl, or $C_3$-$C_8$-halogencycloalkyl, each of which having 1 to 9 halogen atoms selected from the group consisting of fluorine, chlorine and bromine, or
- $R^7$ and $R^8$, together with the nitrogen atom to which they are bonded, form a saturated heterocycle having 5 to 8 ring atoms, wherein the heterocycle is optionally substituted with one or more identical or different substituents selected from the group consisting of halogen and $C_1$-$C_4$-alkyl, in which the heterocycle optionally has 1 or 2 additional, non-adjacent heteroatoms selected from the group consisting of oxygen, sulphur and NR$^{11}$,
- $R^9$ and $R^{10}$, independently of one another, are hydrogen, $C_1$-$C_8$-alkyl, or $C_3$-$C_8$-cycloalkyl; or $C_1$-$C_8$-halogenalkyl or $C_3$-$C_8$-halogencycloalkyl, each of which having 1 to 9 halogen atoms selected from the group consisting of fluorine, chlorine and bromine, or
- $R^9$ and $R^{10}$, together with the nitrogen atom to which they are bonded, form a saturated heterocycle having 5 to 8 ring atoms, wherein the heterocycle is optionally substituted with one or more identical or different substituents selected from the group consisting of halogen and $C_1$-$C_4$-alkyl, in which the heterocycle optionally has 1 or 2 additional, non-adjacent heteroatoms selected from the group consisting of oxygen, sulphur and NR$^{11}$, and
- $R^{11}$ is hydrogen or $C_1$-$C_6$-alkyl.

2. The compound according to claim 1, where
- $R^1$ is hydrogen, fluorine, chlorine, bromine, amino, $C_1$-$C_4$-alkylamino, di($C_1$-$C_4$-alkyl)amino, cyano, methyl, ethyl or $C_1$-$C_2$-halogenalkyl having 1 to 5 halogen atoms selected from the group consisting of fluorine, chlorine and bromine, $R^2$ is fluorine, chlorine, bromine, methyl, ethyl or $C_1$-$C_2$-halogenalkyl having 1 to 5 halogen atoms selected from the group consisting of fluorine, chlorine and bromine, $R^3$ is hydrogen, $C_1$-$C_6$-alkyl, $C_1$-$C_4$-alkylsulphonyl, $C_1$-$C_3$-alkoxy-$C_1$-$C_3$-alkyl, or $C_3$-$C_6$-cycloalkyl; $C_1$-$C_4$-halogenalkyl, $C_1$-$C_4$-halogenalkylthio, $C_1$-$C_4$-halogenalkylsulphinyl, $C_1$-$C_4$-halogenalkylsulphonyl, halogen-$C_1$-$C_3$-alkoxy-$C_1$-$C_3$-alkyl, or $C_3$-$C_8$-halogencycloalkyl, each of which having 1 to 9 halogen atoms selected from the group consisting of fluorine, chlorine and bromine; formyl, formyl-$C_1$-$C_3$-alkyl, ($C_1$-$C_3$-alkyl)carbonyl-$C_1$-$C_3$-alkyl, or ($C_1$-$C_3$-alkoxy)carbonyl-$C_1$-$C_3$-alkyl; halogen-($C_1$-$C_3$-alkyl)-carbonyl-$C_1$-$C_3$-alkyl, or halogen-($C_1$-$C_3$-alkoxy)carbonyl-$C_1$-$C_3$-alkyl, each of which having 1 to 13 halogen atoms selected from the group consisting of fluorine, chlorine and bromine; ($C_1$-$C_6$-alkyl)carbonyl, ($C_1$-$C_4$-alkoxy)carbonyl, ($C_1$-$C_3$-alkoxy-$C_1$-$C_3$-alkyl)carbonyl, or ($C_3$-$C_6$-cycloalkyl)carbonyl; ($C_1$-$C_4$-halogenalkyl)carbonyl, ($C_1$-$C_4$-halogenalkoxy)carbonyl, (halogen-$C_1$-$C_3$-alkoxy-$C_1$-$C_3$-alkyl)carbonyl, or ($C_3$-$C_6$-halogencycloalkyl)carbonyl, each of which having 1 to 9 halogen atoms selected from the group consisting of fluorine, chlorine and bromine; or —C(=O)C(=O)$R^6$, —CONR$^7$R$^8$ or —CH$_2$NR$^9$R$^{10}$, $R^4$ is fluorine, chlorine, methyl, iso-propyl, methoxy, methylthio or trifluoromethyl, $R^5$ is fluorine, chlorine, bromine, cyano, nitro, amino, hydroxy, formyl, methyl, ethyl, n-propyl, iso-propyl, n-butyl, iso-butyl, sec-butyl, tert-butyl, vinyl, allyl, methoxy, ethoxy, n-propoxy, iso-propoxy, vinyloxy, allyloxy, methylthio, ethylthio, n-propylthio, iso-propylthio, methylsulphinyl, ethylsulphinyl, n-propylsulphinyl, iso-propylsulphinyl, methylsulphonyl, ethylsulphonyl, n-propylsulphonyl, iso-propylsulphonyl, methoxymethyl, methoxyethyl, ethoxymethyl, ethoxyethyl, methylthiomethyl, methylthioethyl, ethylthiomethyl, ethylthioethyl, methylamino, ethylamino, iso-propylamino, dimethylamino, diethylamino, dipropylamino, diisopropylamino, methylcarbonyl, ethylcarbonyl, methylaminocarbonyl, dimethylaminocarbonyl, methylcarbonylamino, methylcarbonylmethylamino, cyclopropyl, cyclopropyloxy, trifluoromethyl, trichloromethyl, trifluoroethyl, difluoromethoxy, trifluoromethoxy, difluorochloromethoxy, trifluoroethoxy, difluoromethylthio, difluorochloromethylthio or trifluoromethylthio, or $R^5$ is $C_2$-$C_4$-alkenylene optionally substituted with one or two substituents selected from the group consisting of fluorine, chlorine, bromine, methyl, ethyl, n-propyl, iso-propyl, n-butyl, iso-butyl, sec-butyl, tert-butyl, and trifluoromethyl, when two $R^5$ moieties are in the ortho position to each other, n is 2, 3 or 4, wherein the $R^5$ moieties can be the same or different, $R^6$ is hydrogen, $C_1$-$C_6$-alkyl, $C_1$-$C_4$-alkoxy, $C_1$-$C_3$-alkoxy-$C_1$-$C_3$-alkyl, or $C_3$-$C_6$-cycloalkyl; or $C_1$-$C_4$-halogenalkyl, $C_1$-$C_4$-halogenalkoxy, halogen-$C_1$-$C_3$-alkoxy-$C_1$-$C_3$-alkyl, or $C_3$-$C_6$-halogencycloalkyl, each of which having 1 to 9 halogen atoms selected from the group consisting of fluorine, chlorine and bromine, $R^7$ and $R^8$, independently of one another, each are hydrogen, $C_1$-$C_6$-alkyl, $C_1$-$C_3$-alkoxy-$C_1$-$C_3$-alkyl, or $C_3$-$C_6$-cycloalkyl; or $C_1$-$C_4$-halogenalkyl, halogen-$C_1$-$C_3$-alkoxy-$C_1$-$C_3$-alkyl, or $C_3$-$C_6$-halogencycloalkyl, each of which having 1 to 9 halogen atoms selected from the group consisting of fluorine, chlorine and bromine, or $R^7$ and $R^8$, together with the nitrogen atom to which they are bonded, form a saturated heterocycle having 5 or 6 ring atoms, wherein the heterocycle is optionally substituted with one to four identical or different substituents selected from the group consisting of halogen and $C_1$-$C_4$-alkyl, in which the heterocycle optionally has 1 or 2 additional, non-adjacent heteroatoms selected from the group consisting of oxygen, sulphur and NR$^{11}$, $R^9$ and $R^{10}$, independently of one another, are hydrogen, $C_1$-$C_6$-alkyl, or $C_3$-$C_6$-cycloalkyl; or $C_1$-$C_4$-halogenalkyl or $C_3$-$C_6$-halogencycloalkyl, each of which having 1 to 9 halogen atoms selected from the group consisting of fluorine, chlorine and bromine, or $R^9$ and $R^{10}$, together with the nitrogen atom to which they are bonded, form a saturated heterocycle having 5 or 6 ring atoms, wherein the heterocycle is optionally substituted with one to four identical or different substituents selected from the group consisting of halogen and $C_1$-$C_4$-alkyl, in which the heterocycle optionally has 1 or 2 additional, non-adjacent heteroatoms selected from the group consisting of oxygen, sulphur and NR$^{11}$, and $R^{11}$ is hydrogen or $C_1$-$C_4$-alkyl.

3. A method for preparing a compound of (I) according to claim 1, comprising (a) Reacting a Carboxylic Acid Derivative of Formula (II)

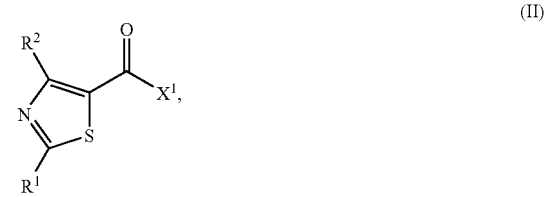

where $R^1$ and $R^2$ are as defined in claim 1 and $X^1$ is halogen or hydroxy, with a biphenyl amine of Formula (III)

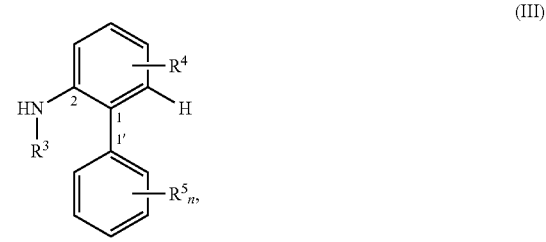

$R^3$, $R^4$, $R^5$ and n are as defined in claim 1, optionally in the presence of a catalyst, optionally in the presence of a condensation agent, optionally in the presence of an acid binding agent and optionally in the presence of a diluent, or (b) Reacting a Halogen Carboxamide of Formula (Iv)

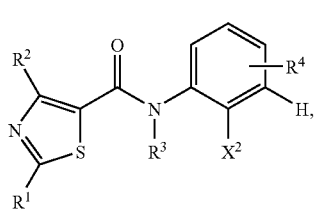

(IV)

where
$R^1$, $R^2$, $R^3$ and $R^4$ are as defined in claim 1,
$X^2$ is bromine, iodine or trifluoromethylsulphonate,
with a boronic acid derivative of Formula (V)

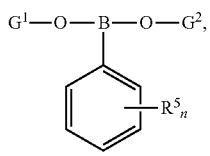

(V)

where
$R^5$ and n are as defined in claim 1 and
$G^1$ and $G^2$ each is hydrogen or together form tetramethylethylene,
in the presence of a catalyst, optionally in the presence of an acid binding agent and optionally in the presence of a diluent, or (c) reacting a boronic acid derivative of Formula (VI)

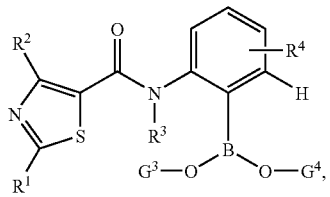

(VI)

where
$R^1$, $R^2$, $R^3$ and $R^4$ are as defined in claim 1, and
$G^3$ and $G^4$ each is hydrogen or together form tetramethylethylene,
with a phenyl derivative of Formula (VII)

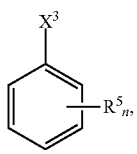

(VII)

where
$R^5$ and n are as defined in claim 1 and
$X^3$ is chlorine, bromine, iodine or trifluoromethylsulphonate,
in the presence of a catalyst, optionally in the presence of an acid binding agent and optionally in the presence of a diluent, or (d) Reacting a Halogen Carboxamide of Formula (IV)

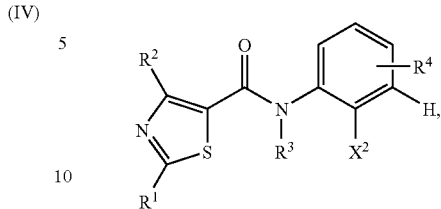

(IV)

where
$R^1$, $R^2$, $R^3$ and $R^4$ are as defined in claim 1, and
$X^2$ is bromine, iodine or trifluoromethylsulphonate,
with a phenyl derivative of Formula (VII)

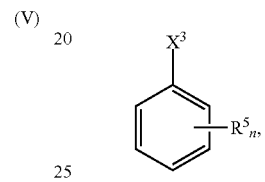

(VII)

where
$R^5$ and n are as defined in claim 1 and
$X^3$ is chlorine, bromine, iodine or trifluoromethylsulphonate,
in the presence of a palladium or nickel catalyst and in the presence of 4,4,4',4',5,5,5',5'-octamethyl-2,2'-bis-1,3,2-dioxaborolane, optionally in the presence of an acid binding agent and optionally in the presence of a diluent, or (e) Reacting a Biphenyl Thiazole Carboxamide of Formula (I-a)

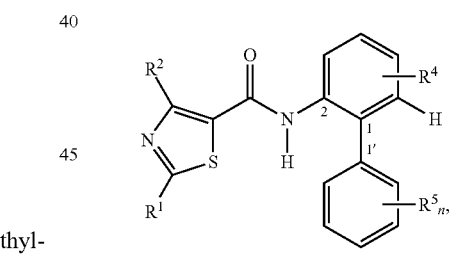

(I-a)

where
$R^1$, $R^2$, $R^4$, $R^5$ and n are as defined in claim 1,
with a halogenide of Formula (VIII)

$R^{3A}$—$X^4$ (VIII), where
$R^{3A}$ is $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, or $C_3$-$C_8$-cycloalkyl; $C_1$-$C_6$-halogenalkyl, $C_1$-$C_4$-halogenalkylthio, $C_1$-$C_4$-halogenalkylsulphinyl, $C_1$-$C_4$-halogenalkylsulphonyl, halogen-$C_1$-$C_4$-alkoxy-$C_1$-$C_4$-alkyl, or $C_3$-$C_8$-halogencycloalkyl, each of which having 1 to 9 halogen atoms selected from the group consisting of fluorine, chlorine and bromine; formyl, formyl-$C_1$-$C_3$-alkyl, ($C_1$-$C_3$-alkyl)carbonyl-$C_1$-$C_3$-alkyl, or ($C_1$-$C_3$-alkoxy)carbonyl-$C_1$-$C_3$-alkyl; halogen-($C_1$-$C_3$-alkyl)carbonyl-$C_1$-$C_3$-alkyl or halogen-($C_1$-$C_3$-alkoxy)carbonyl-$C_1$-$C_3$- alkyl, each of which having 1 to 13 halogen atoms selected from the group consisting of fluorine, chlorine and bromine; $(C_1$-$C_8$-alkyl)carbonyl, $(C_1$-$C_8$-alkoxy)carbonyl, $(C_1$-$C_4$-alkoxy-$C_1$-$C_4$-alkyl)carbonyl, or $(C_3$-$C_8$-cycloalkyl)carbonyl; or $(C_1$-$C_6$-halogenalkyl)carbonyl, $(C_1$-$C_6$-halogenalkoxy)carbonyl, (halogen-$C_1$-$C_4$-alkoxy-$C_1$-$C_4$-alkyl)carbonyl, or $(C_3$-$C_8$-halogencycloalkyl)carbonyl, each of which having 1 to 9 halogen atoms selected from the group consisting of fluorine, chlorine and bromine; or —C(=O)C(=O)$R^6$, —CONR$^7$R$^8$ or —CH$_2$NR$^9$R$^{10}$, R$^6$, R$^7$, R$^8$, R$^9$ and R$^{10}$ are as defined in claim 1, and X$^4$ is chlorine, bromine or iodine, in the presence of a base and in the presence of a diluent.

4. The compound according to claim 1 wherein R$^4$ is fluorine.

5. The compound according to claim 4 wherein R$^4$ is fluorine in the 3-position or in the 5-position.

6. The compound according to claim 4 wherein R$^4$ is fluorine in the 5-position.

7. The compound according to claim 1 wherein R$^4$ is chlorine.

8. The compound according to claim 7 wherein R$^4$ is chlorine in the 4-position.

9. The compound according to claim 7 wherein R$^4$ is chlorine in the 5-position.

10. The compound according to claim 1 wherein R$^4$ is trifluoromethyl.

11. The compound according to claim 10 wherein R$^4$ is trifluoromethyl in the 4-position.

12. The compound according to claim 11 wherein R$^4$ is trifluoromethyl in the 5-position.

13. The compound according to claim 1 wherein R$^4$ is methoxy or methylthio.

14. The compound according to claim 13 wherein R$^4$ is methoxy or methylthio in the 3-position.

15. The compound according to claim 13 wherein R$^4$ is methoxy or methylthio in the 5-position.

16. The compound according to claim 1 wherein R$^4$ is methyl.

17. The compound according to claim 16 wherein R$^4$ is methyl in the 4-position.

18. The compound according to claim 16 wherein R$^4$ is methyl in the 5-position.

19. The compound according to claim 1 wherein R$^4$ is isopropyl.

20. The compound according to claim 19 wherein R$^4$ is isopropyl in the 4-position.

21. The compound according to claim 19 wherein R$^4$ is isopropyl in the 5-position.

22. The compound according to claim 1 wherein n is 2, 3, or 4 wherein the R$^5$ moieties can be the same or different.

23. The compound according to claim 22 wherein n is 2 or 3 and wherein the R$^5$ moieties can be the same or different.

24. The compound according to claim 22 wherein n is 2 and wherein the R$^5$ moieties can be the same or different.

25. The compound according to claim 22 wherein n is 2 and wherein the R$^5$ moieties are the same.

26. The compound according to claim 22 wherein n is 2 and wherein the R$^5$ moieties are different.

27. The compound according to claim 22 wherein R$^5$ is fluorine, chlorine, bromine, methyl, trifluoromethyl, difluoromethoxy, or trifluoromethoxy.

28. The compound according to claim 24 wherein R$^5$ is fluorine, chlorine, bromine, methyl, trifluoromethyl, difluoromethoxy, or trifluoromethoxy.

29. The compound according to claim 24 wherein the R$^5$ moieties are in the 3',4' position, the 2',4' position, the 3',5' position or the 2',5'-position.

30. The compound according to claim 25 wherein the R$^5$ moieties are in the 3',4' position, the 2',4' position, the 3',5' position or the 2',5'-position.

31. The compound according to claim 26 wherein the R$^5$ moieties are in the 3',4' position, the 2',4' position, the 3',5' position or the 2',5'-position.

32. The compound according to claim 25 wherein the R$^5$ moiety is chlorine.

33. The compound according to claim 25 wherein the R$^5$ moiety is fluorine.

34. The compound according to claim 26 wherein the R$^5$ moieties are chlorine and fluorine.

* * * * *